United States Patent
McGowan et al.

(10) Patent No.: US 11,819,229 B2
(45) Date of Patent: Nov. 21, 2023

(54) BALLOON SURFACE PHOTOACOUSTIC PRESSURE WAVE GENERATION TO DISRUPT VASCULAR LESIONS

(71) Applicant: Boston Scientific Scimed, Inc., Maple Grove, MN (US)

(72) Inventors: Roger W. McGowan, Otsego, MN (US); Daniel Frank Massimini, Brooklyn Park, MN (US); Haiping Shao, Plymouth, MN (US); Christopher Smuk, Champlin, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 329 days.

(21) Appl. No.: 16/884,257

(22) Filed: May 27, 2020

(65) Prior Publication Data
US 2020/0397453 A1 Dec. 24, 2020

Related U.S. Application Data

(60) Provisional application No. 62/863,506, filed on Jun. 19, 2019.

(51) Int. Cl.
*A61B 17/22* (2006.01)
*A61B 18/24* (2006.01)
(Continued)

(52) U.S. Cl.
CPC ........ *A61B 17/2202* (2013.01); *A61B 18/245* (2013.01); *A61B 2017/22051* (2013.01);
(Continued)

(58) Field of Classification Search
CPC .......... A61B 2017/22051; A61B 2017/22062; A61B 2017/22069; A61B 17/22004–22029
See application file for complete search history.

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 1/2022
AU 2019452180 1/2022
(Continued)

OTHER PUBLICATIONS

International Search Report and Written Opinion dated Sep. 11, 2020 in PCT Application Serial No. PCT/US2020038517.
(Continued)

*Primary Examiner* — Darwin P Erezo
*Assistant Examiner* — Brigid K Byrd
(74) *Attorney, Agent, or Firm* — ROEDER & BRODER LLP; James P. Broder

(57) ABSTRACT

A photoacoustic catheter adapted for placement within a blood vessel having a vessel wall includes an elongate shaft, a balloon and a photoacoustic transducer. The elongate shaft can extend from a proximal region to a distal region. The elongate shaft can include a light guide that is configured to be placed in optical communication with a light source. The balloon is coupled to the elongate shaft, and can be configured to expand from a collapsed configuration suitable for advancing the photoacoustic catheter through a patient's vasculature to a first expanded configuration suitable for anchoring the photoacoustic catheter in position relative to a treatment site. The photoacoustic transducer can be disposed on a surface of the balloon and in optical communication with the light guide. The photoacoustic transducer can include a light-absorbing material and a thermal expansion material.

20 Claims, 14 Drawing Sheets

(51) Int. Cl.
  *A61B 90/30* (2016.01)
  *A61B 18/00* (2006.01)
  *A61B 18/22* (2006.01)

(52) U.S. Cl.
  CPC ............... *A61B 2017/22062* (2013.01); *A61B 2017/22069* (2013.01); *A61B 2018/0022* (2013.01); *A61B 2018/00255* (2013.01); *A61B 2018/2261* (2013.01); *A61B 2018/2294* (2013.01); *A61B 2090/306* (2016.02)

(56) References Cited

U.S. PATENT DOCUMENTS

| | | | |
|---|---|---|---|
| 4,799,479 A * | 1/1989 | Spears | A61M 25/104 606/7 |
| 4,913,142 A | 4/1990 | Kittrell et al. | |
| 4,932,954 A | 6/1990 | Wondrazek et al. | |
| 4,955,895 A | 9/1990 | Sugiyama | |
| 4,960,108 A | 10/1990 | Reichel et al. | |
| 4,994,059 A | 2/1991 | Kosa et al. | |
| 5,034,010 A | 7/1991 | Kittrell et al. | |
| 5,041,121 A | 8/1991 | Wondrazek et al. | |
| 5,104,391 A | 4/1992 | Ingle | |
| 5,104,392 A | 4/1992 | Kittrell et al. | |
| 5,116,227 A | 5/1992 | Levy | |
| 5,152,768 A | 10/1992 | Bhatta | |
| 5,173,049 A | 12/1992 | Levy | |
| 5,181,921 A | 1/1993 | Makita et al. | |
| 5,200,838 A | 4/1993 | Nudelman | |
| 5,290,277 A | 3/1994 | Vercimak et al. | |
| 5,324,282 A | 6/1994 | Dodick | |
| 5,372,138 A | 12/1994 | Crowley | |
| 5,387,225 A | 2/1995 | Euteneur | |
| 5,400,428 A | 3/1995 | Grace | |
| 5,422,926 A | 6/1995 | Smith | |
| 5,454,809 A | 10/1995 | Janssen | |
| 5,509,917 A | 4/1996 | Cecchetti | |
| 5,540,679 A | 7/1996 | Fram | |
| 5,562,657 A | 10/1996 | Griffin | |
| 5,598,494 A | 1/1997 | Behrmann et al. | |
| 5,609,606 A | 3/1997 | O'Boyle | |
| 5,611,807 A | 3/1997 | O'Boyle | |
| 5,697,377 A | 12/1997 | Wittkampf | |
| 5,718,241 A | 2/1998 | Ben-Haim et al. | |
| 5,729,583 A | 3/1998 | Tang | |
| 5,772,609 A | 6/1998 | Nguyen et al. | |
| 5,860,974 A * | 1/1999 | Abele | A61B 8/12 606/41 |
| 5,891,135 A * | 4/1999 | Jackson | A61B 18/1492 606/41 |
| 5,906,611 A | 5/1999 | Dodick et al. | |
| 5,944,687 A | 8/1999 | Benett et al. | |
| 6,015,404 A | 1/2000 | Altshuler | |
| 6,080,119 A | 6/2000 | Schwarze et al. | |
| 6,123,923 A | 9/2000 | Unger | |
| 6,139,510 A | 10/2000 | Palermo | |
| 6,186,963 B1 | 2/2001 | Schwarze et al. | |
| 6,203,537 B1 | 3/2001 | Adrian | |
| 6,210,404 B1 | 4/2001 | Shadduck | |
| 6,339,470 B1 | 1/2002 | Papademetriou et al. | |
| 6,368,318 B1 | 4/2002 | Visuri et al. | |
| 6,500,174 B1 | 12/2002 | Maguire et al. | |
| 6,514,203 B2 | 2/2003 | Bukshpan | |
| 6,514,249 B1 | 2/2003 | Maguire | |
| 6,524,251 B2 | 3/2003 | Rabiner et al. | |
| 6,538,739 B1 | 3/2003 | Visuri et al. | |
| 6,607,502 B1 | 8/2003 | Maguire et al. | |
| 6,652,547 B2 | 11/2003 | Rabiner et al. | |
| 6,666,834 B2 | 12/2003 | Restle et al. | |
| 6,773,447 B2 | 8/2004 | Laguna | |
| 6,849,994 B1 | 2/2005 | White et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,309,324 B2 | 12/2007 | Hayes et al. | |
| 7,470,240 B2 | 12/2008 | Schultheiss et al. | |
| 7,569,032 B2 | 8/2009 | Naimark et al. | |
| 7,599,588 B2 | 10/2009 | Eberle et al. | |
| 7,713,260 B2 | 5/2010 | Essard | |
| 7,758,572 B2 | 7/2010 | Weber et al. | |
| 7,810,395 B2 | 10/2010 | Zhou | |
| 7,850,685 B2 | 12/2010 | Kunis et al. | |
| 7,867,178 B2 | 1/2011 | Simnacher | |
| 7,972,299 B2 | 7/2011 | Carter | |
| 7,985,189 B1 | 7/2011 | Ogden et al. | |
| 8,162,859 B2 | 4/2012 | Schultheiss et al. | |
| 8,166,825 B2 | 5/2012 | Zhou | |
| 8,192,368 B2 | 6/2012 | Woodruff | |
| 8,292,913 B2 | 10/2012 | Warnack | |
| 8,328,820 B2 | 12/2012 | Diamant | |
| 3,364,235 A1 | 1/2013 | Kordis et al. | |
| 8,419,613 B2 | 4/2013 | Saadat | |
| 8,439,890 B2 | 5/2013 | Beyar | |
| 8,556,813 B2 | 10/2013 | Cashman et al. | |
| 8,574,247 B2 | 11/2013 | Adams et al. | |
| 8,657,814 B2 | 2/2014 | Werneth | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 8,986,339 B2 | 3/2015 | Warnack | |
| 8,992,817 B2 | 3/2015 | Stamberg | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,131,949 B2 | 9/2015 | Coleman et al. | |
| 9,138,249 B2 | 9/2015 | Adams et al. | |
| 9,138,260 B2 | 9/2015 | Miller et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,289,132 B2 | 3/2016 | Ghaffari et al. | |
| 9,289,224 B2 | 3/2016 | Adams et al. | |
| 9,320,530 B2 | 4/2016 | Grace | |
| 9,333,000 B2 | 5/2016 | Hakala et al. | |
| 9,375,223 B2 | 6/2016 | Wallace | |
| 9,421,025 B2 | 8/2016 | Hawkins et al. | |
| 9,433,428 B2 | 9/2016 | Hakala et al. | |
| 9,504,809 B2 | 11/2016 | Bo | |
| 9,510,887 B2 | 12/2016 | Burnett | |
| 9,522,012 B2 | 12/2016 | Adams | |
| 9,554,815 B2 | 1/2017 | Adams et al. | |
| 9,555,267 B2 | 1/2017 | Ein-gal | |
| 9,566,209 B2 | 2/2017 | Katragadda et al. | |
| 9,579,114 B2 | 2/2017 | Mantell et al. | |
| 9,629,567 B2 | 4/2017 | Porath et al. | |
| 9,642,673 B2 | 5/2017 | Adams | |
| 9,662,069 B2 | 5/2017 | De Graff et al. | |
| 9,687,166 B2 | 6/2017 | Subramaniam | |
| 9,730,715 B2 | 8/2017 | Adams | |
| 9,764,142 B2 | 9/2017 | Imran | |
| 9,814,476 B2 | 11/2017 | Adams et al. | |
| 9,861,377 B2 | 1/2018 | Mantell et al. | |
| 9,867,629 B2 | 1/2018 | Hawkins et al. | |
| 9,894,756 B2 | 2/2018 | Weinkam et al. | |
| 9,955,946 B2 | 5/2018 | Miller et al. | |
| 9,974,963 B2 | 5/2018 | Imran | |
| 9,974,970 B2 | 5/2018 | Nuta et al. | |
| 9,993,292 B2 | 6/2018 | Adams et al. | |
| 10,039,561 B2 | 8/2018 | Adams et al. | |
| 10,136,829 B2 | 11/2018 | Deno et al. | |
| 10,149,690 B2 | 12/2018 | Hawkins et al. | |
| 10,159,505 B2 | 12/2018 | Takala et al. | |
| 10,194,994 B2 | 2/2019 | Deno et al. | |
| 10,201,387 B2 | 2/2019 | Grace et al. | |
| 10,206,698 B2 | 2/2019 | Hakala et al. | |
| 10,226,265 B2 | 3/2019 | Ku et al. | |
| 10,357,264 B2 | 7/2019 | Kat-Kuoy | |
| 10,405,923 B2 | 9/2019 | Yu et al. | |

(56) References Cited

U.S. PATENT DOCUMENTS

| | | | |
|---|---|---|---|
| 10,406,031 B2 | 9/2019 | Thyzel |
| 10,420,569 B2 | 9/2019 | Adams |
| 10,441,300 B2 | 10/2019 | Hawkins |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 2001/0016761 A1 | 8/2001 | Rudie |
| 2001/0051784 A1 | 12/2001 | Brisken |
| 2002/0045811 A1 | 4/2002 | Kittrell et al. |
| 2002/0065512 A1* | 5/2002 | Fjield ................ A61B 17/2202 606/27 |
| 2002/0082553 A1 | 6/2002 | Duchamp |
| 2002/0183729 A1 | 12/2002 | Farr et al. |
| 2002/0188204 A1* | 12/2002 | McNamara ........ A61B 1/00183 600/478 |
| 2003/0009157 A1 | 1/2003 | Evine et al. |
| 2003/0050632 A1 | 3/2003 | Fjield et al. |
| 2003/0065316 A1 | 4/2003 | Evine et al. |
| 2003/0114901 A1 | 6/2003 | Loeb et al. |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Ane et al. |
| 2004/0249401 A1 | 12/2004 | Rabiner |
| 2004/0254570 A1* | 12/2004 | Hadjicostis .......... A61B 8/4416 606/27 |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Esh |
| 2005/0273014 A1 | 12/2005 | Gianchandani et al. |
| 2005/0277839 A1 | 12/2005 | Alderman et al. |
| 2006/0033241 A1* | 2/2006 | Schewe .............. B29C 49/4823 264/402 |
| 2006/0084966 A1 | 4/2006 | Maguire et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0299392 A1 | 12/2007 | Beyar et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1* | 5/2008 | Zhou ...................... A61B 8/12 606/7 |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0299327 A1 | 12/2009 | Tilson et al. |
| 2009/0306533 A1 | 12/2009 | Rousche |
| 2009/0312768 A1* | 12/2009 | Hawkins .......... A61B 17/22022 606/128 |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1* | 10/2011 | Vrba .................... A61B 18/18 604/93.01 |
| 2011/0275990 A1 | 11/2011 | Besser et al. |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Derscher et al. |
| 2012/0116289 A1 | 5/2012 | Tawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |

(56) References Cited

U.S. PATENT DOCUMENTS

| | | |
|---|---|---|
| 2013/0116714 A1 | 5/2013 | Adams et al. |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0336632 A1 | 11/2014 | Toth |
| 2014/0357997 A1 | 12/2014 | Hartmann |
| 2015/0005576 A1 | 1/2015 | Diodone et al. |
| 2015/0039002 A1 | 2/2015 | Hawkins |
| 2015/0073430 A1 | 3/2015 | Hakala et al. |
| 2015/0080875 A1 | 3/2015 | Kasprzyk et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Tawkins et al. |
| 2016/0143522 A1 | 5/2016 | Ransbury |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1* | 6/2016 | Grace .................. A61B 18/26 606/7 |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0092763 A1 | 4/2018 | Dagan et al. |
| 2018/0098779 A1 | 4/2018 | Betelia et al. |
| 2018/0152568 A1 | 6/2018 | Kat-kuoy |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Ggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0175111 A1 | 6/2019 | Genereux et al. |
| 2019/0175300 A1 | 6/2019 | Horn |
| 2019/0175372 A1 | 6/2019 | Boydan et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0365400 A1 | 12/2019 | Adams et al. |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046949 A1 | 2/2020 | Chisena et al. |
| 2020/0054352 A1* | 2/2020 | Brouillette ....... A61B 17/22012 |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |

(56) References Cited

U.S. PATENT DOCUMENTS

| | | | |
|---|---|---|---|
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Aser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |
| CN | 106794043 | 3/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 P | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | 1992008515 A2 | 5/1992 |
| WO | 9902095 A1 | 1/1999 |
| WO | 9920189 A1 | 4/1999 |
| WO | WO200067648 | 11/2000 |
| WO | WO2000067648 A1 | 11/2000 |
| WO | 2001003599 A1 | 1/2001 |
| WO | 2006006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 2011126580 A2 | 10/2011 |
| WO | WO2012025833 | 3/2012 |
| WO | WO20120052924 A1 | 4/2012 |
| WO | WO2012099974 A2 | 7/2012 |
| WO | WO20120120495 A1 | 9/2012 |
| WO | WO2013119662 | 8/2013 |
| WO | 20130169807 A1 | 11/2013 |
| WO | WO2013169807 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 2015177790 A1 | 11/2015 |
| WO | WO2016089683 A1 | 6/2016 |
| WO | WO2016090175 | 6/2016 |
| WO | WO2016109739 | 7/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 2018175322 A1 | 9/2018 |
| WO | WO2018175322 | 9/2018 |
| WO | WO2018191013 | 10/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |

(56) References Cited

FOREIGN PATENT DOCUMENTS

| WO | WO20200086361 | A1 | 4/2020 |
|---|---|---|---|
| WO | WO2020089876 | A1 | 5/2020 |
| WO | WO2020157648 | | 8/2020 |
| WO | WO2020256898 | | 12/2020 |
| WO | WO2020256898 | A1 | 12/2020 |
| WO | WO2020256949 | | 12/2020 |
| WO | WO2020256949 | A1 | 12/2020 |
| WO | WO2020263469 | A1 | 12/2020 |
| WO | WO2020263685 | A1 | 12/2020 |
| WO | WO2020263687 | A1 | 12/2020 |
| WO | WO2020263688 | A1 | 12/2020 |
| WO | WO2020263689 | A1 | 12/2020 |
| WO | WO2021061451 | | 4/2021 |
| WO | WO2021067563 | | 4/2021 |
| WO | 2021086571 | A1 | 5/2021 |
| WO | 2021101766 | A1 | 5/2021 |
| WO | WO2021096922 | A1 | 5/2021 |
| WO | WO2021101766 | | 5/2021 |
| WO | WO2021126762 | A1 | 6/2021 |
| WO | WO2021162855 | A1 | 8/2021 |
| WO | WO2021173417 | A1 | 9/2021 |
| WO | WO2021183367 | A1 | 9/2021 |
| WO | WO2021183401 | A1 | 9/2021 |
| WO | WO2021188233 | A1 | 9/2021 |
| WO | WO2021202248 | A1 | 10/2021 |
| WO | WO2021231178 | A1 | 11/2021 |
| WO | WO2021247685 | A1 | 12/2021 |
| WO | WO2021257425 | A1 | 12/2021 |
| WO | WO2022007490 | | 1/2022 |
| WO | WO2022008440 | | 1/2022 |
| WO | WO2022010767 | A1 | 1/2022 |
| WO | WO2022055784 | | 3/2022 |
| WO | WO2022125525 | | 6/2022 |
| WO | WO2022154954 | | 7/2022 |
| WO | WO2022173719 | | 8/2022 |
| WO | WO2022187058 | | 9/2022 |
| WO | WO2022216488 | | 10/2022 |
| WO | WO2022240674 | | 11/2022 |
| WO | WO2022260932 | | 12/2022 |

OTHER PUBLICATIONS

International Search Report and Written Opinion dated Sep. 9, 2020 in PCT Application Serial No. PCT/US2020038530.
International Search Report and Written Opinion dated Sep. 11, 2020 in PCT Application Serial No. PCT/US2020038521.
International Search Report and Written Opinion dated Sep. 7, 2020 in PCT Application Serial No. PCT/US2020034642.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser Induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, p. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, dated Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.

(56) References Cited

OTHER PUBLICATIONS

International Search Report and Written Opinion dated Jun. 22, 2018, in Application Serial No. NL2019807, issued by the European Patent Office.

International Search Report and Written Opinion dated Feb. 19, 2021 in PCT Application Serial No. PCT/US2020/059960.

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh. "Three dimensional mapping of atrial fibrillation: techniques and necessity." Journal of interventional cardiac electrophysiology 13.1 (2005): 53-59.

Shariat, Mohammad Hassan. Processing the intracardiac electrogram for atrial fibrillation ablation. Diss. Queen's University (Canada), 2016.

Meng et al., "Accurate Recovery of Atrial Endocardial Potential Maps From Non-contact Electrode Data." Auckland Bioengineering Institute. (ID 1421).

Jiang et al., "Multielectrode Catheter For Substrate Mapping for Scar-related VT Ablation: A Comparison Between Grid Versus Linear Configurations." UChicago Medicine, Center for Arrhythmia Care, Chicago IL (ID 1368).

Sacher et al., "Comparison of Manual Vs Automatic Annotation to Identify Abnormal Substrate for Scar Related VT Ablation." LIRYC Institute, Bordeaux University Hospital, France (ID 1336).

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.

Chen, Sung-Liang, "Review of Laser-Generated Ultrasound Transmitters and their Applications to All-Optical Ultrasound Transducers and Imaging", Appl. Sci. 2017, 7, 25.

Colchester, R., et al. "Laser-Generated ultrasound with optica fibres using functionalised carbon nanotube composite coatings", Appl. Phys. Lett., 2014, vol. 104, 173504, American Institute of Physics.

Poduval, R., et al. "Optical fiber ultrasound transmitter with electrospun carbon nanotube-polymer composite", Appl. Phys. Lett., 2017, vol. 110, 223701, American Institute of Physics.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001, SPIE.

International Search Report and Written Opinion dated Jan. 3, 2020, in PCT Application Serial No. PCT/US2019/056579.

Communication Pursuant to Article 94(3) EPC, for European Patent Application No. 18185152.8, dated Jan. 16, 2019.

European Search Report, for European Patent Application No. 18185152.8, dated Dec. 20, 2018.

Schafter+Kirchhoff, Laser Beam Couplers series 60SMS for coupling into single-mode and polarization-maintaining fiber cables, Schafter+Kirchhoff, pp. 1-5, Germany.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion, issued by the European Patent Office for PCT/2021/XXX, dated Sep. 30, 2021.

International Search Report and Written Opinion dated Jul. 29, 2020 in PCT Application Serial No. PCT/US2020/034005.

Provisional International Search Report and Written Opinion dated Feb. 19, 2021 in PCT Application Serial No. PCT/US2020/059960.

Oriel Instruments, "Introduction to Beam Splitters for Optical Research Applications", Apr. 2014, pp. 1-9, https://www.azoptics.com/Article.aspx?ArticaID=871.

International Search Report and Written Opinion dated Apr. 12, 2021 in PCT Application Serial No. PCT/US2020/059960.

International Search Report and Written Opinion dated Apr. 13, 2021 in PCT Application Serial No. PCT/US2020/064846.

International Search Report and Written Opinion dated Apr. 13, 2021 in PCT Application Serial No. PCT/US2021/013944.

International Search Report and Written Opinion dated May 25, 2021 in PCT Application Serial No. PCT/US2021/017604.

International Search Report and Written Opinion, issued by the EP/ISA, in PCT/US2021/048819, dated Jan. 14, 2022.

Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

(56) References Cited

OTHER PUBLICATIONS

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and on Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method for Fabricating Artificial Kidney Stones of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions,Theory, and Implications for aser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Coming, NY, USA.

(56) References Cited

OTHER PUBLICATIONS

Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones for Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", asers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 677-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies a Subsidiary of Molex, Nov. 2007.
Iang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'Nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work on a Sub-Millimeter Spark-Gap For Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015. (This reference was cited in a prior Information Disclosure Statement. However, the relevant date was missing. The date has now been added.).
Medlight, "Cylindircal light diffuser Model RD", Medlight S.A., Switzerland. 2015. (This reference was cited in a prior Information Disclosure Statement. However, the relevant date was missing. The date has now been added.).

(56) References Cited

OTHER PUBLICATIONS

OHL, Siew-Wan, et al. "Bubbles with shock waves and ultrasound: a review", Interface Focus, pp. 1-15, vol. 5, The Royal Society Publishing. Oct. 2015. (This reference was cited in a prior Information Disclosure Statement. However, the relevant date was missing. The date has now been added.).
Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).
Meng et al., "Accurate Recovery of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).
Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
International Search Report and Written Opinion dated Aug. 25, 2022 in PCT Application Serial No. PCTUS/2022/028035.
International Search Report and Written Opinion dated Sep. 15, 2022 in PCT Application Serial No. PCTUS/2022/032045.
International Search Report and Written Opinion, PCT Application Serial No. PCT/US2022/047751 dated Feb. 10, 2023, by the European Patent Office. (56PCT).
International Search Report and Written Opinion dated Nov. 8, 2022 in PCT Application Serial No. PCTUS/2022/039678.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023. (Re 45PCT).
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023. (Re 57PCT).

\* cited by examiner

BALLOON SURFACE PHOTOACOUSTIC PRESSURE WAVE GENERATION TO DISRUPT VASCULAR LESIONS

RELATED APPLICATION

This application claims priority on U.S. Provisional Application Ser. No. 62/863,506, filed on Jun. 19, 2019, and entitled "BALLOON SURFACE PHOTOACOUSTIC SHOCKWAVE GENERATION TO DISRUPT VASCULAR LESIONS". To the extent permitted, the contents of U.S. Provisional Application Ser. No. 62/863,506 are incorporated in their entirety herein by reference.

BACKGROUND

Vascular lesions within blood vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

In a first aspect, a photoacoustic catheter adapted for placement within a blood vessel having a vessel wall is provided. The photoacoustic catheter can have an elongate shaft extending from a proximal region to a distal region. The elongate shaft can include a light guide, where the light guide can be configured to be placed in optical communication with a light source. The photoacoustic catheter can include a balloon coupled to the elongate shaft, where the balloon can be configured to expand from a collapsed configuration suitable for advancing the photoacoustic catheter through a patient's vasculature to a first expanded configuration suitable for anchoring the photoacoustic catheter in position relative to a treatment site. The photoacoustic catheter can include a photoacoustic transducer disposed on a surface of the balloon and in optical communication with the light guide. The photoacoustic transducer can include a light-absorbing material and a thermal expansion material.

In a second aspect, in addition to one or more of the preceding or following aspects, or in the alternative to some aspects, the photoacoustic transducer is located on an outer surface of the balloon.

In a third aspect, in addition to one or more of the preceding or following aspects, or in the alternative to some aspects, the photoacoustic transducer is located on an inner surface of the balloon.

In a fourth aspect, in addition to one or more of the preceding or following aspects, or in the alternative to some aspects, the photoacoustic transducer includes a conformal coating on the surface of the balloon extending continuously from a proximal location to distal location and extending continuously around a circumference of the balloon.

In a fifth aspect, in addition to one or more of the preceding or following aspects, or in the alternative to some aspects, the photoacoustic transducer can be configured as a plurality of circumferential bars, longitudinal bars, diagonal bars, or islands.

In a sixth aspect, in addition to one or more of the preceding or following aspects, or in the alternative to some aspects, a distal portion of the light guide includes a diffraction grating pattern configured to, when the balloon is in the first expanded configuration, direct light from the light guide to one or more light pattern locations.

In a seventh aspect, in addition to one or more of the preceding or following aspects, or in the alternative to some aspects, a wall of the balloon includes integrated fluid bubbles.

In an eighth aspect, in addition to one or more of the preceding or following aspects, or in the alternative to some aspects, the balloon can be configured to change from a first expanded configuration to a second, further expanded configuration.

In a ninth aspect, in addition to one or more of the preceding or following aspects, or in the alternative to some aspects, the balloon includes a stress concentration structure and the photoacoustic transducer is located on a surface of the stress concentration structure.

In a tenth aspect, in addition to one or more of the preceding or following aspects, or in the alternative to some aspects, the stress concentration structure includes a larger diameter region compared to a remainder of an adjacent balloon wall portion, includes a dome structure, or includes a rectangular structure.

In an eleventh aspect, in addition to one or more of the preceding or following aspects, or in the alternative to some aspects, the thermal expansion material of the photoacoustic transducer is a polymer, and where the polymer is in thermal contact with the light absorbing material.

In a twelfth aspect, in addition to one or more of the preceding or following aspects, or in the alternative to some aspects, the thermal expansion material is selected from a group including polydimethylsiloxane (PDMS), polytetrafluoroethylene (PTFE), polyimide, polyisobutylene (FIB), PIB polyurethane, polyurethanes, styrene isoprene butadiene, ethylene propylene polyacrylic, ethylene acrylic, fluorosilicone, polybutadiene, polyisoprene, and thermoplastic elastomers.

In a thirteenth aspect, in addition to one or more of the preceding or following aspects, or in the alternative to some aspects, the light-absorbing material is selected from a group including nanoparticles, carbon nanotubes, candle soot, candle soot nanoparticles, carbon black, a nanotube array, multiwall carbon nanotubes, and light absorbing dye.

In a fourteenth aspect, in addition to one or more of the preceding or following aspects, or in the alternative to some aspects, the light guide is an optical fiber and the light source is a laser.

In a fifteenth aspect, in addition to one or more of the preceding or following aspects, or in the alternative to some aspects, the photoacoustic catheters herein can include an outer balloon surrounding the balloon having the photoacoustic transducer.

In a sixteenth aspect, a photoacoustic catheter adapted for placement within a blood vessel having a vessel wall is provided. The photoacoustic catheter can include an elongate shaft extending from a proximal region to a distal region, where the elongate shaft can include a light guide. The light guide can be configured to be placed in optical communication with a light source. The photoacoustic catheter can include an outer balloon coupled to the elongate shaft, where the outer balloon can be configured to expand from a collapsed configuration suitable for advancing the photoacoustic catheter through a patient's vasculature to a first expanded configuration suitable for anchoring the photoacoustic catheter in position relative to a treatment site. The photoacoustic catheter can further include an inner balloon coupled to the elongate shaft within the outer balloon, the inner balloon configured to expand from a collapsed configuration suitable for advancing the photoacoustic catheter through a patient's vasculature to a first expanded configuration. The inner balloon can include a photoacoustic transducer disposed on a surface of the inner balloon and in optical communication with the light guide. The photoacoustic transducer can include a light-absorbing material and a thermal expansion material. The photoacoustic catheter can be configured to expand the outer balloon using an outer balloon inflation fluid and to expand the inner balloon using an inner balloon inflation fluid.

In a seventeenth aspect, in addition to one or more of the preceding or following aspects, or in the alternative to some aspects, the outer balloon inflation fluid can be a liquid and the inner balloon inflation fluid can be a gas.

In an eighteenth aspect, in addition to one or more of the preceding or following aspects, or in the alternative to some aspects, the inner balloon can be configured to include a concave portion when in the first expanded configuration, the photoacoustic transducer is located on an outer surface of the inner balloon, and the concave portion can be configured to focus at least one acoustic pressure wave from the photoacoustic transducer.

In a nineteenth aspect, a method for photoacoustically generating pressure waves within a blood vessel is provided. The method can include advancing a photoacoustic catheter to a treatment site within the blood vessel, where the photoacoustic catheter can include an elongate shaft, a balloon coupled to the elongate shaft, a light guide, and a photoacoustic transducer disposed on a surface of the balloon. The method can include expanding the balloon from a collapsed configuration suitable for advancing the photoacoustic catheter through a patient's vasculature to a first expanded configuration suitable for anchoring the photoacoustic catheter in position relative to the treatment site. The method can include after expanding the balloon, activating a light source in optical communication with the light guide and the photoacoustic transducer, thereby imparting acoustic pressure waves upon the treatment site.

In a twentieth aspect, in addition to one or more of the preceding or following aspects, or in the alternative to some aspects, the method can further include, after activating the light source, further expanding the balloon from the first expanded configuration to a second further expanded configuration.

In yet another aspect, in addition to one or more of the preceding aspects, or in the alternative to some aspects, the photoacoustic catheter can include a thermal expansion material and a light-absorbing material that are positioned adjacent to one another in layers.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Treatment of vascular lesions can reduce major adverse events or death in affected subjects. A major adverse event is one that can occur anywhere within the body due to the presence of a vascular lesion. Major adverse events can include, but are not limited to major adverse cardiac events, major adverse events in the peripheral or central vasculature, major adverse events in the brain, major adverse events in the musculature, or major adverse events in any of the internal organs.

The systems and methods disclosed herein describe the use of pressure waves for intravascular calcification disruption. In various embodiments herein, the pressure wave generation is accomplished using a photoacoustic catheter adapted for placement within a blood vessel. The photoacoustic catheters include an elongate shaft extending from a proximal region to a distal region. The elongate shafts can include a light guide (also sometimes referred to herein as a "first light guide", "second light guide", etc.) configured to be placed in optical communication with a light source. The photoacoustic catheters can include a balloon coupled to the elongate shaft and can be configured to expand from a collapsed configuration suitable for advancing the photoacoustic catheter through a patient's vasculature to a first expanded configuration suitable for anchoring the photoacoustic catheter in position relative to a treatment site. The balloon includes a photoacoustic transducer disposed on a surface of the balloon and in optical communication with the light guide, where the photoacoustic transducer includes a light-absorbing material and a thermal expansion material.

As used herein, the terms "pressure wave," "acoustic wave," "acoustic pressure wave," or "sound wave" can be used interchangeably, and describe propagating a pressure disturbance in gaseous, liquid, or solid material medium, including vibrational waves, sound waves, ultrasonic waves and acoustic shock waves.

As used herein, the terms "intravascular lesion" or "vascular lesion", can be used interchangeably, and describe any lesion region within or adjacent to a vessel wall.

Figure 1:
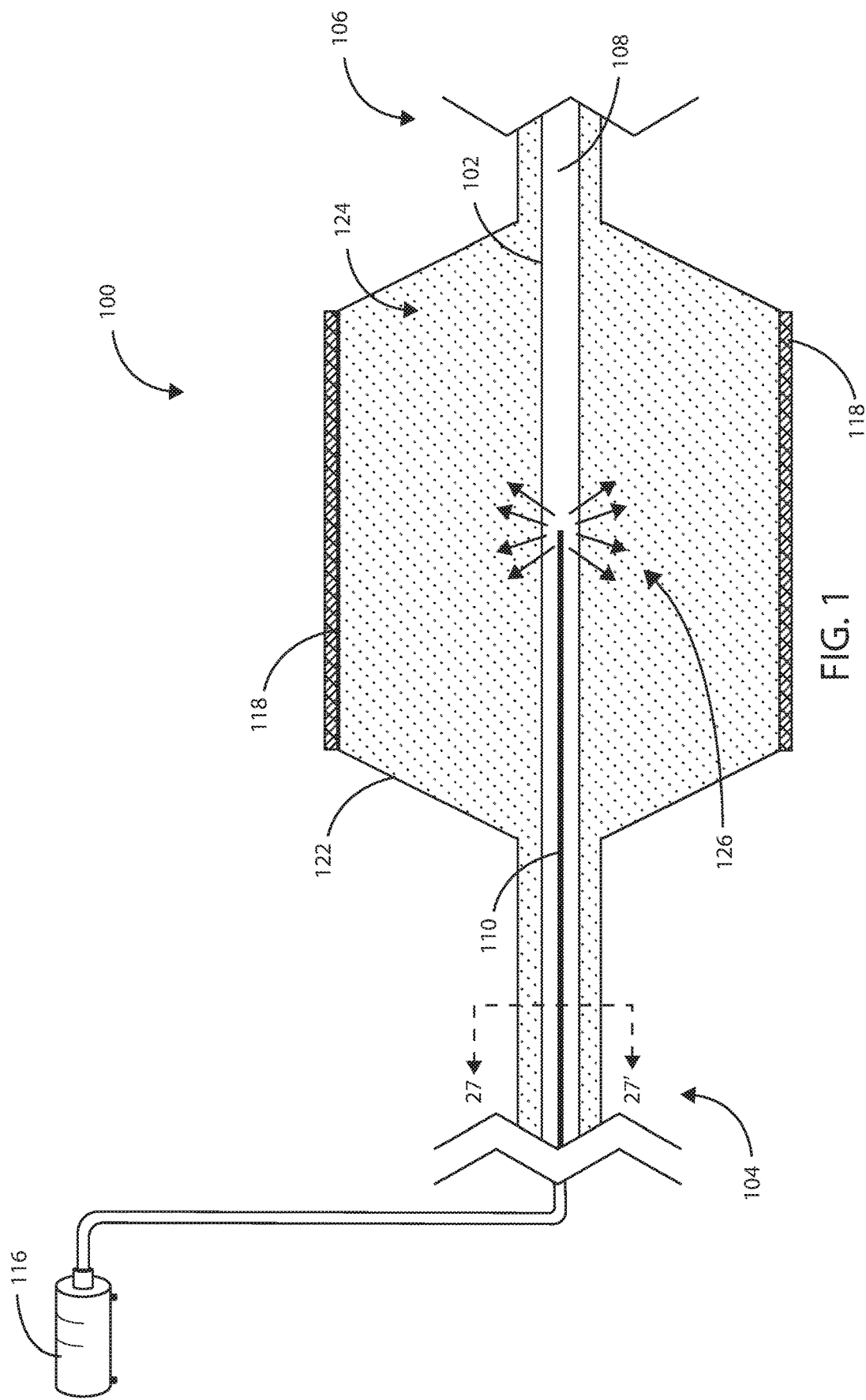
FIG. 1 is a schematic cross-sectional view of a photoacoustic catheter in accordance with various embodiments herein.

It will be appreciated that the photoacoustic catheters herein can include many different forms. Referring now to FIG. 1, a schematic cross-sectional view of a photoacoustic catheter 100 is shown in accordance with various embodiments herein. Photoacoustic catheter 100 can be adapted for placement within a blood vessel having a vessel wall. The photoacoustic catheter 100 can be used to treat a vascular lesion found within or adjacent to the vessel wall. In some embodiments, the vascular lesion can include a calcified vascular lesion. In some embodiments, the vascular lesion can include a fibrous vascular lesion. The photoacoustic catheter 100 can include an elongate shaft 102 extending from a proximal region 104 to a distal region 106, and can also include a lumen 108. In some embodiments, the photoacoustic catheter 100 can have a distal region opening and can accommodate and be tracked over a guide wire to a treatment location. In some embodiments, the photoacoustic catheter 100 does not include a lumen. In embodiments where the elongate shaft 102 does not include a lumen to be accessed by a caregiver, the elongate shaft 102 can be configured to allow the catheter to be steered through a patient's vasculature.

The elongate shaft 102 of photoacoustic catheter 100 can be coupled to a (also sometimes referred to herein simply as a "light guide") 110 in optical communication with a light source 116. In some embodiments, the first light guide 110 can be an optical fiber and the light source can be a laser. The light source 116 can be in optical communication with the first light guide 110 at a proximal region 104 of the elongate shaft 102. A schematic depiction of exemplary emitted light 126 as transmitted by the first light guide 110 is shown. It will be appreciated that, photoacoustic catheter 100 can include more than one light guide. In some embodiments, photoacoustic catheter 100 can include a second light guide, a third light guide, a fourth light guide, a fifth light guide, a sixth light guide, or more. In some embodiments, a plurality of light guides will be evenly spaced and radially offset from each other so that where there are n light guides, they are spaced apart by 360 degrees divided by n. In other embodiments, the light guides will be unevenly spaced and radially offset from each other.

It will be appreciated that the photoacoustic catheters herein can include any number of light guides. For example, in some embodiments, the photoacoustic catheters herein can include from one light guide to five light guides. In other embodiments, the photoacoustic catheters herein can include from five to fifteen light guides. In yet other embodiments, the photoacoustic catheters herein can include from ten light guides to thirty light guides. The photoacoustic catheters herein can include one, two, three, four, five, six, seven, eight, nine, or ten light guides. The photoacoustic catheters can include 11, 12, 13, 14, 15, 16, 17, 18, 19, 20, 21, 22, 23, 24, 25, 26, 27, 28, 29, or 30 light guides. It will be appreciated that photoacoustic catheters herein can include any number of light guides that can fall within a range, wherein any of the forgoing numbers can serve as the lower or upper bound of the range, provided that the lower bound of the range is a value less than the upper bound of the range. In some embodiments, the photoacoustic catheters herein can include more than 30 light guides.

Figure 2:
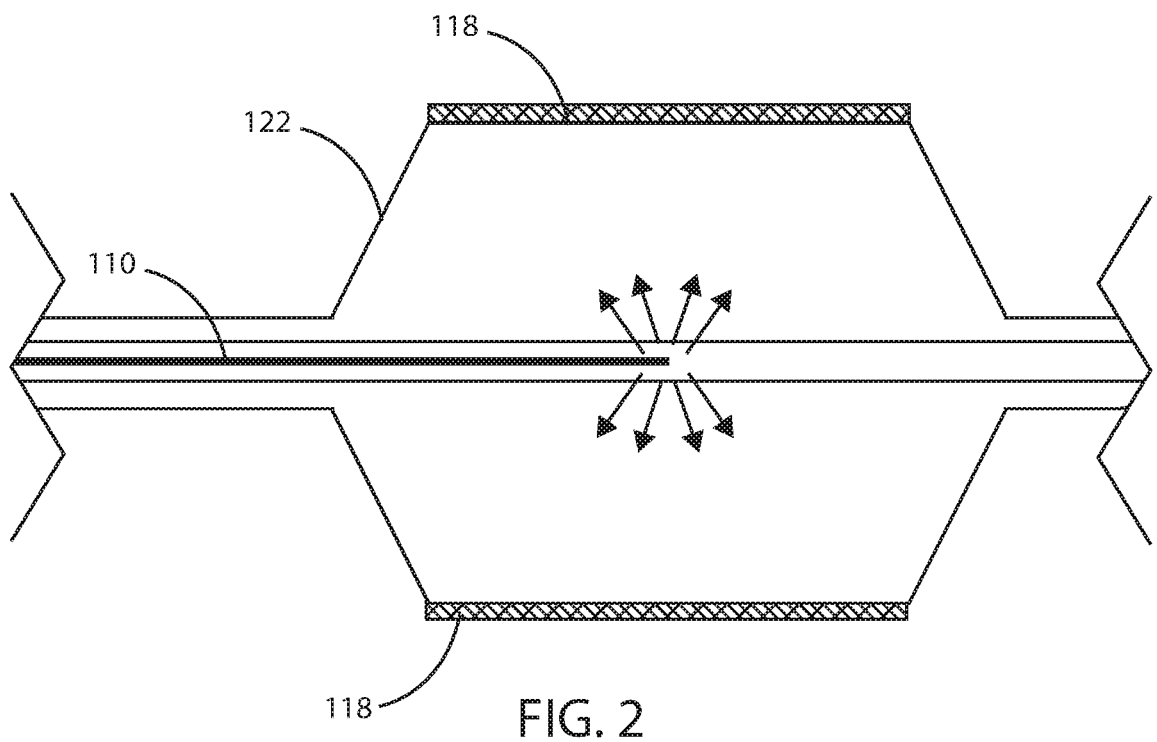
FIG. 2 is a schematic cross-sectional view of a photoacoustic catheter in accordance with various embodiments herein.
Figure 3:
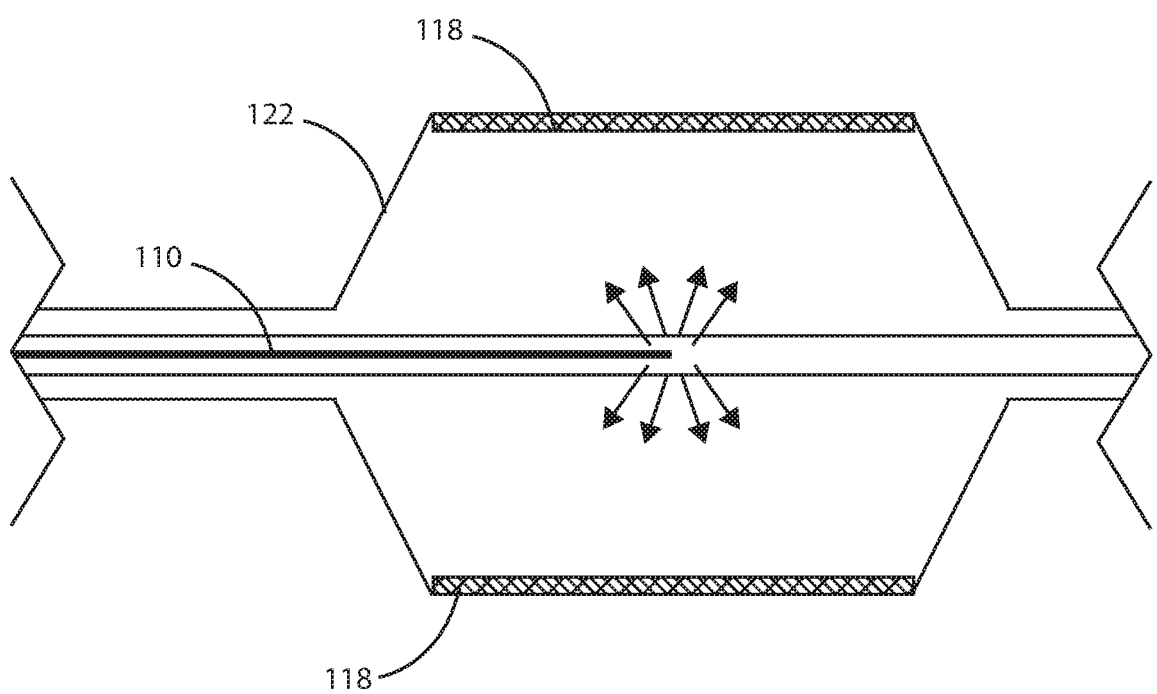
FIG. 3 is a schematic cross-sectional view of a photoacoustic catheter in accordance with various embodiments herein.
Figure 4:
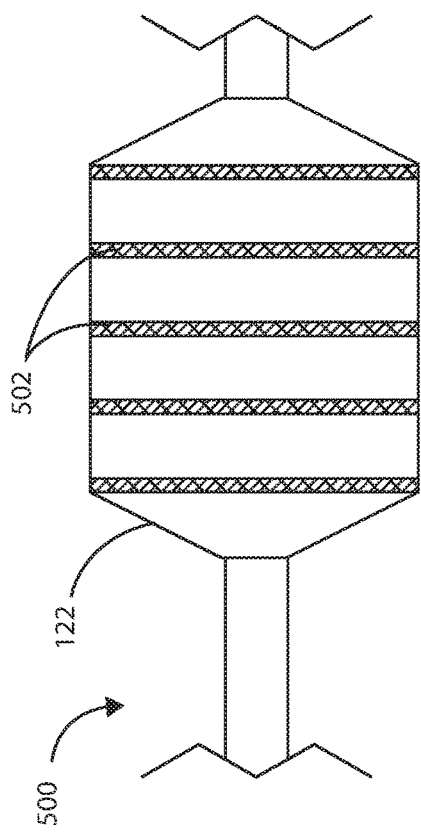
FIG. 4 is a schematic side-plan view of a photoacoustic catheter in accordance with various embodiments herein.
Figure 5:
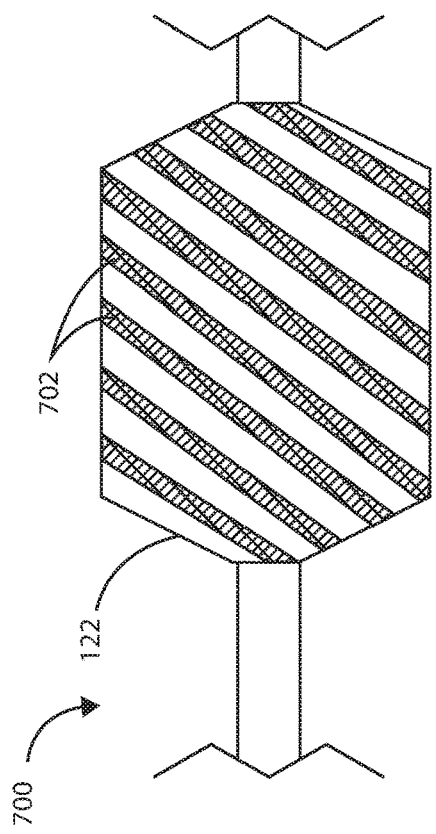
FIGS. 5-7 are schematic side-plan views of additional configurations of the photoacoustic catheter in accordance with various embodiments herein.
Figure 6:
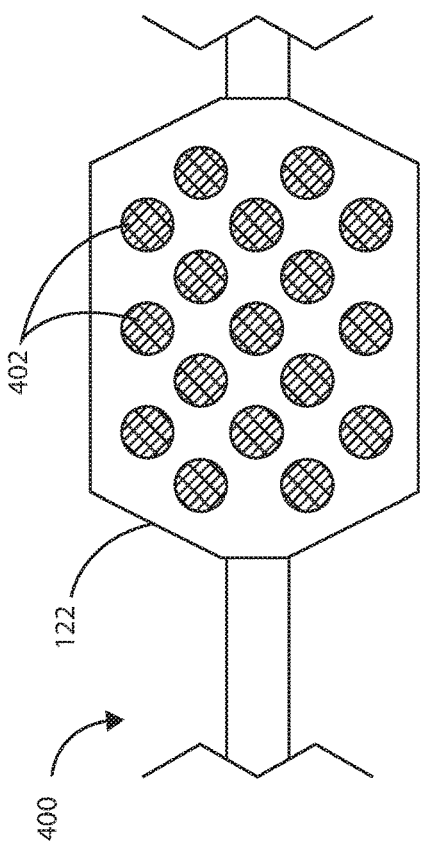
Figure 7:
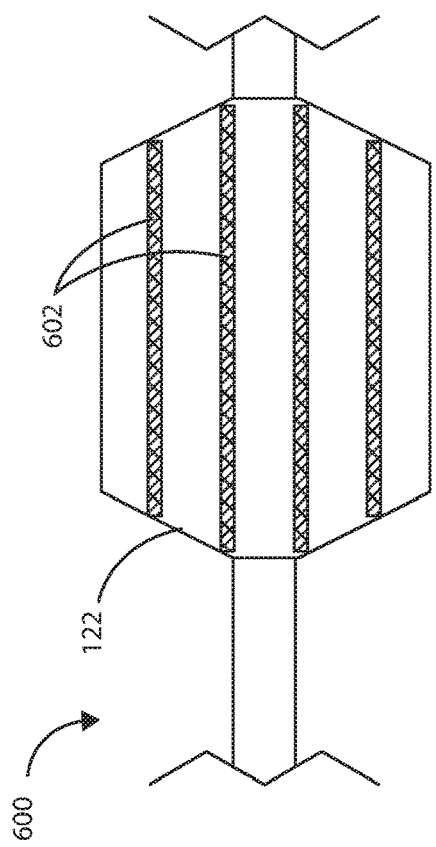

The photoacoustic catheter 100 includes a balloon 122. The balloon 122 can expand from a collapsed configuration suitable for advancing the catheter through a patient's vasculature to a first expanded configuration suitable for anchoring the catheter in position relative to a treatment site. Expansion of the balloons herein to various expanded configurations will be discussed in more detail below. The balloon 122 includes a photoacoustic transducer 118 disposed on a surface of the balloon 122 and in optical communication with the first light guide 110 to direct light 126 to the interior of balloon 122. In some embodiments, the photoacoustic transducer 118 is disposed on an outer surface of the balloon 122, as shown in FIG. 2. In other embodiments, the photoacoustic transducer 118 is disposed on an inner surface of the balloon 122, as shown in FIG. 3. The balloon 122 can be an inflatable balloon. In some embodiments, photoacoustic catheter 100 also includes an outer balloon that can surround balloon 122, where the photoacoustic transducer is disposed on balloon 122. In some embodiments, the balloon 122 is configured to change from a first expanded configuration to a second, further expanded configuration. It will be appreciated that the balloons herein can assume multiple expanded configurations between a first expanded configuration and a second further expanded configuration. In some embodiments, the balloons herein will include a maximum expanded configuration.

The photoacoustic transducer 118 can be adapted to impart acoustic pressure waves upon a calcified lesion to induce fractures in the calcified lesion. The photoacoustic transducer 118 can be formed from a light-absorbing material and a thermal expansion material. In some embodiments, the thermal expansion material of the photoacoustic transducer 118 is a polymer, and the polymer is in thermal contact with the light absorbing material. The thermal expansion material and the light absorbing material will both be discussed in more detail below. The balloon 122 can be inflated by introduction of a balloon inflation fluid 124. The balloon inflation fluid 124 can include a fluid suitable for transmitting acoustic energy from the first light guide 110 to an inside surface of the balloon 122. Exemplary balloon inflation fluids can include, but are not to be limited to one or more of water, saline, contrast medium, gases such as carbon dioxide, and the like. The balloon inflation fluids suitable for use herein can be tailored on the basis of composition, viscosity, density, and the like in order to manipulate the rate of travel of the acoustic pressure waves therein.

The photoacoustic transducer can be conformal and continuous on at least a portion of a surface of the balloon. In some embodiments, the photoacoustic transducer includes a conformal coating on a surface of the balloon 122 extending continuously from a proximal location to distal location and extending continuously around a circumference of the balloon 122, as shown in FIGS. 1-3.

Referring now to FIGS. 4-7, schematic side-plan views of exemplary conformal and non-continuous photoacoustic transducer patterns are shown in accordance with various embodiments herein. The configuration of photoacoustic catheter 400 in FIG. 4 includes a photoacoustic transducer pattern having a plurality of islands 402 of the photoacoustic transducer disposed on a surface of the balloon 122. The islands can include, but are not to be limited to shapes including circles, ovals, diamonds, squares, rectangles, triangles, stars, symbols, letters, logos, and the like. The configuration of photoacoustic catheter 500 in FIG. 5 includes a photoacoustic transducer pattern of circumferential bars 502. The configuration of photoacoustic catheter 600 in FIG. 6 includes a photoacoustic transducer pattern of longitudinal bars 602. The configuration of photoacoustic catheter 700 in FIG. 7 includes a photoacoustic transducer pattern of diagonal bars 702. It will be appreciated that the continuous and non-continuous photoacoustic transducers described herein can be disposed on an external surface of the balloon or on an internal surface of the balloon. The conformal and non-continuous photoacoustic transducer examples of FIGS. 4-7 can be referred to as each including a single photoacoustic transducer that includes separate portions or as including a plurality of photoacoustic transducers, such as a first photoacoustic transducer and one or more of a second photoacoustic transducer, a third photoacoustic transducer, a fourth photoacoustic transducer, a fifth photoacoustic transducer, a sixth photoacoustic transducer, a seventh photoacoustic transducer, an eighth photoacoustic transducer, a ninth photoacoustic transducer, a tenth photoacoustic transducer, etc.

Figure 8:
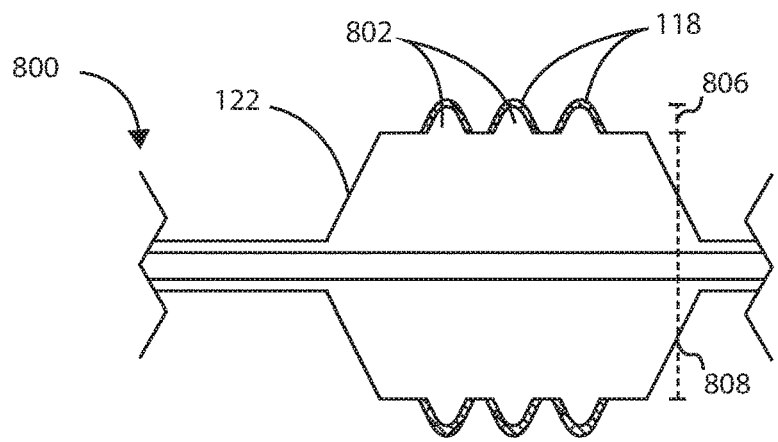
FIG. 8 is a schematic cross-sectional view of a photoacoustic catheter in accordance with various embodiments herein.
Figure 9:
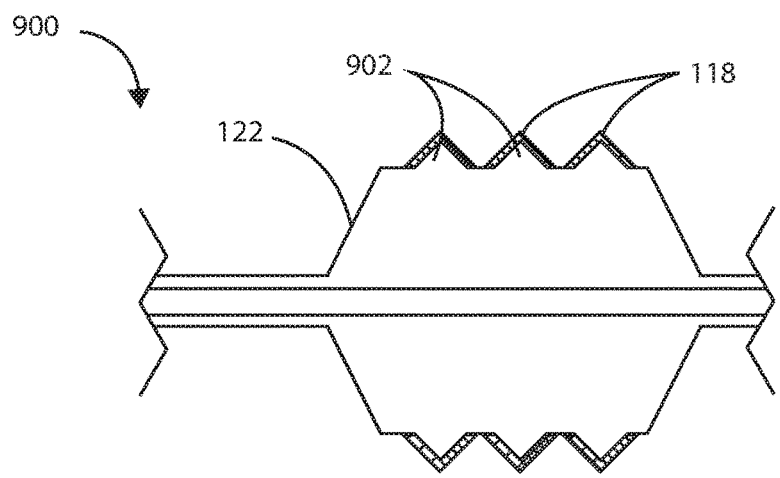
FIG. 9 is a schematic cross-sectional view of a photoacoustic catheter in accordance with various embodiments herein.
Figure 10:
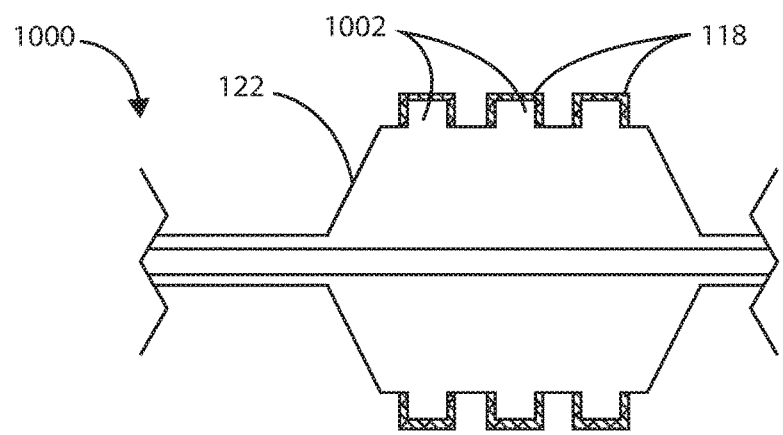
FIG. 10 is a schematic cross-sectional view of a photoacoustic catheter in accordance with various embodiments herein.

The photoacoustic transducer can be localized on various structures on a surface of the balloon 122. Referring now to FIGS. 8-10, schematic cross-sectional views of balloons with stress concentration structures disposed about the circumference are shown in accordance with various embodiments herein. The stress concentration structures can include a variety of shapes and sizes. The stress concentration structures can be made from a metal, a polymeric material, and the like. In some embodiments, the stress concentration structures can be integral to the balloon material. In some embodiments, the stress concentration structures can be attached to the balloon material.

The configuration of photoacoustic catheter 800 in FIG. 8 includes a stress concentration structure having a dome-shaped structure 802 in cross section. The configuration of photoacoustic catheter 900 in FIG. 9 includes a stress concentration structure having a triangle-shaped structure 902 (FIG. 9) in cross section. The configuration of photoacoustic catheter 1000 in FIG. 10 includes a stress concentration structure having a rectangular-shaped structure 1002 (FIG. 10) in cross section. The stress concentration structure can be integral to the balloon or can be physically distinct from the balloon. The stress concentration structure can be made from the same material as the balloon or can be made from a different material than the balloon. In the case of a physically distinct stress concentration structure, the stress concentration structure can be affixed to the surface of the balloon. In various embodiments, the stress concentration structures can be made using a contiguous balloon such that the balloon material can have different properties at different locations to form the stress concentration structures. For example, the balloon material can be more concentrated or of a different composition at different locations about the balloon to form the stress concentrations structures. By way of example, the stress concentration structures 802 of FIG. 8 can be formed integral with the balloon at different locations along or about the balloon.

In some examples, photoacoustic catheters having stress concentration structures include a photoacoustic transducer located on a surface of the stress concentration structure, such as an inner surface of the stress concentration structure or an outer surface of the stress concentration structure, which are shown in FIGS. 8-10. Referring now to FIG. 8, a schematic cross-sectional view of a photoacoustic catheter 800 is shown in accordance with various embodiments herein. The configuration of photoacoustic catheter 800 in FIG. 8 includes a stress concentration structure having a dome-shaped structure 802 on the outer surface of balloon 122 with a photoacoustic transducer 118 disposed on an outer surface of the stress concentration structure. The configuration of photoacoustic catheter 900 in FIG. 9 includes a stress concentration structure having a triangle-shaped structure 902 on the outer surface of balloon 122 with a photoacoustic transducer 118 disposed on an outer surface of the stress concentration structure. The configuration of photoacoustic catheter 1000 in FIG. 10 includes a stress concentration structure having a rectangular-shaped structure 1002 on the outer surface of balloon 122 with a photoacoustic transducer 118 disposed on an outer surface of the stress concentration structure.

It will be appreciated that the stress concentration structures include those having a larger diameter region compared to a remainder of an adjacent balloon wall portion. Referring to FIG. 8, the stress concentration structure can include those that have a height 806 extending in a direction perpendicular to an outer surface of the balloon, where balloon 122 has a diameter 808. Various diameters suitable for use with the balloons herein are described below. The stress concentration structures shown in FIGS. 9 and 10 also include a height extending in a direction perpendicular to an outer surface of the balloon, such that the stress concentration structures have a larger diameter region compared to a remainder of an adjacent balloon wall portion, as discussed in reference to FIG. 8. While not shown in FIGS. 8-10, it will be appreciated that the balloons herein can further include those having stress concentration structures on the outside of the balloon or incorporated into the balloon itself, and a photoacoustic transducer disposed on an inner surface of the balloon. By way of example, the balloon 122 of FIG. 3 could include stress concentration structures disposed on the outer surface of balloon 122 and the photoacoustic transducer 118 disposed on the inner surface. In some embodiments, the photoacoustic transducer disposed on an inner surface of the balloon 122 can conform to the shape of the stress concentration structures on the outer surface.

The stress concentration structures herein can include those that have a height 806 extending in a direction perpendicular to an outer surface of the balloon of from 1 micrometer (μm) to 500 μm. In some embodiments, the stress concentration structure can include those that have a height 806 extending in a direction perpendicular to an outer surface of the balloon of from 75 μm to 200 μm. In some embodiments, the stress concentration structure can include those that have a height 806 extending in a direction perpendicular to an outer surface of the balloon of from 1 μm to 50 μm. In some embodiments, the height 806 of the stress concentrator can be greater than or equal to 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, or 500 μm, or can be an amount falling within a range between any of the foregoing.

Figure 11:
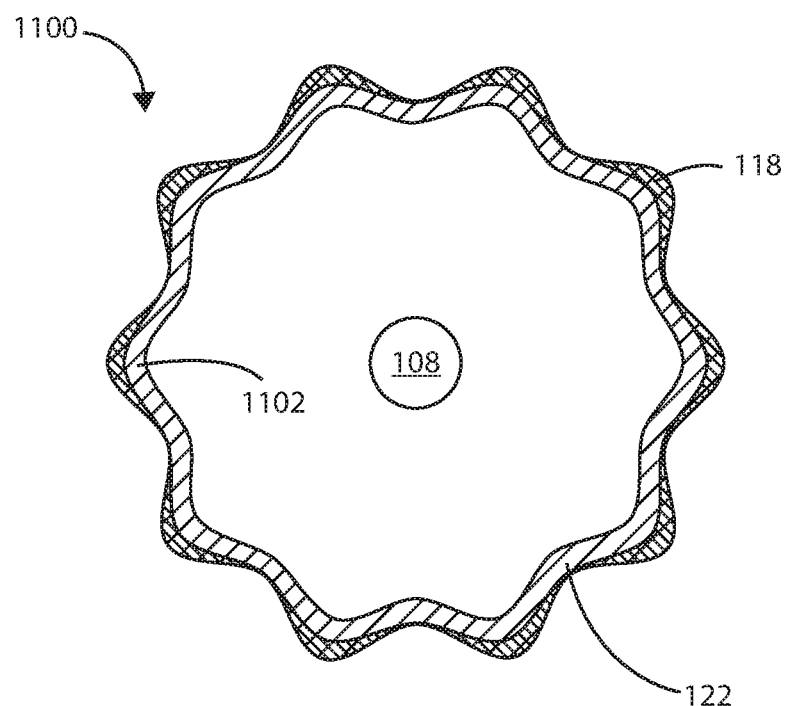
FIG. 11 is a schematic cross-sectional view of a photoacoustic catheter in accordance with various embodiments herein.
Figure 12:
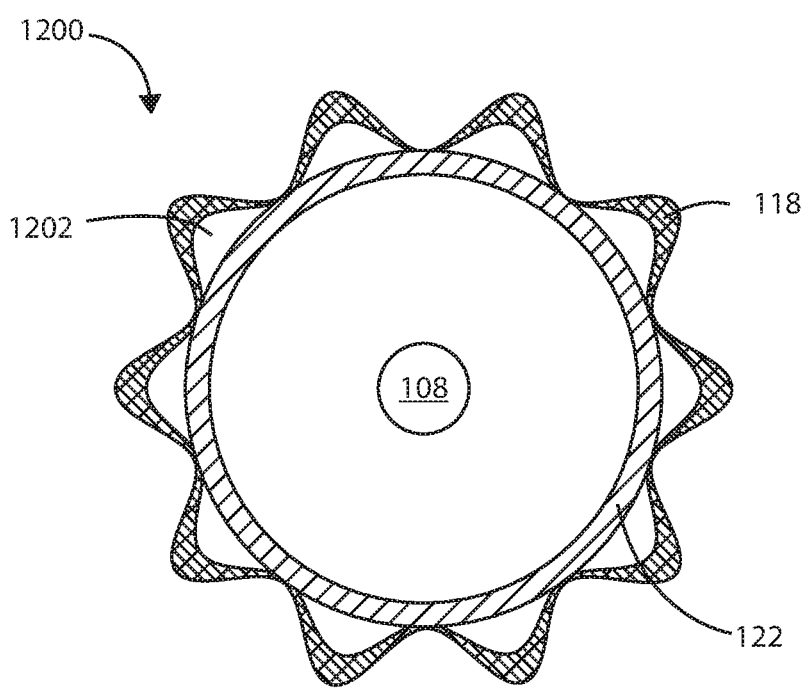
FIG. 12 is a schematic cross-sectional view of a photoacoustic catheter in accordance with various embodiments herein.

The photoacoustic transducer can also be localized along the longitudinal axis of balloon 122. Referring now to FIGS. 11-12, schematic cross-sectional views of balloons with a stress concentration structures disposed along the longitudinal axis are shown in accordance with various embodiments herein. The configuration of photoacoustic catheter 1100 in FIG. 11 includes balloon 122 surrounding a lumen 108 and stress concentration structures 1102 integrated into the balloon 122. A photoacoustic transducer 118 is disposed on the outer surface of the stress concentration structures 1102. The balloon 122 of photoacoustic catheter 1100 includes a variable inner diameter owing to the presence of the stress concentration structures 1102 that are integrated with the balloon 122. The configuration of photoacoustic catheter 1200 in FIG. 12 includes balloon 122 surrounding a lumen 108 and stress concentration structures 1202 affixed to the exterior of the balloon 122. A photoacoustic transducer 118 is disposed on the outer surface of the stress concentration structures 1202. The balloon 122 of 1200 includes a uniform inner diameter.

Figure 13:
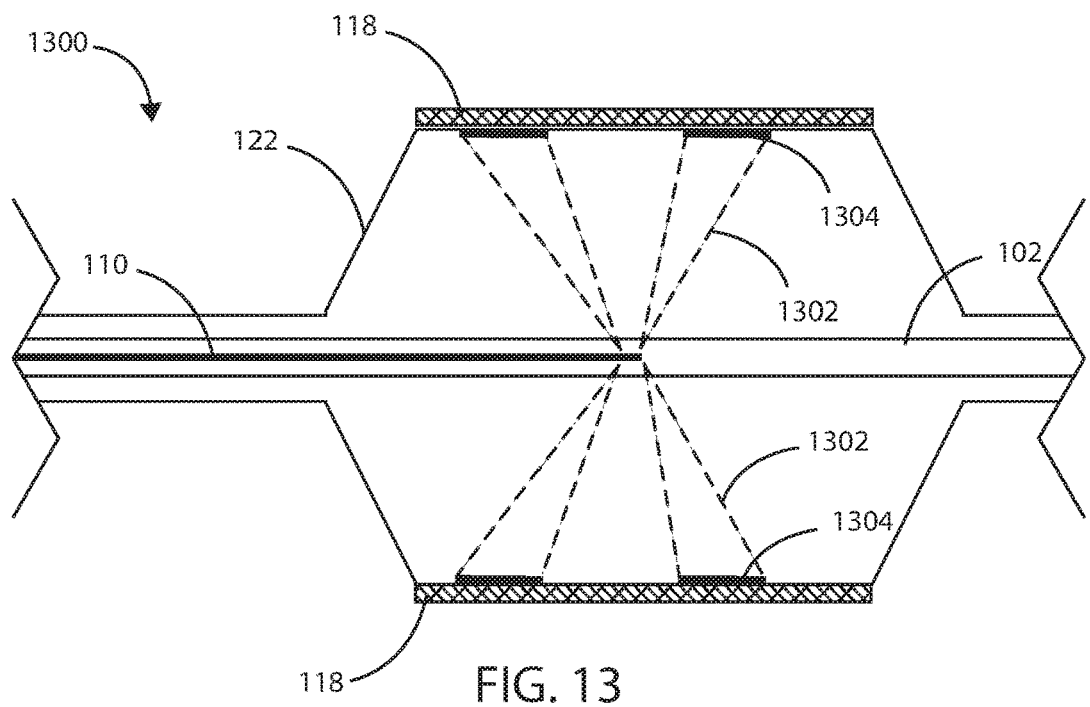
FIG. 13 is a schematic cross-sectional view of a photoacoustic catheter in accordance with various embodiments herein.
Figure 14:
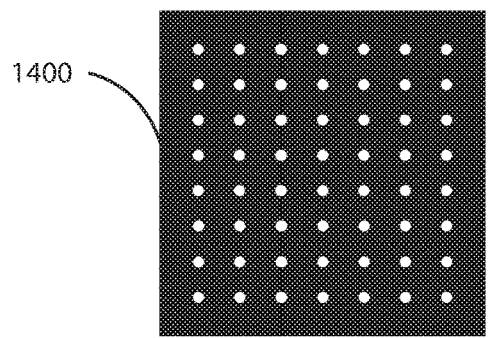
FIG. 14 is a schematic diagram of a light pattern formed by a diffraction grating in accordance with various embodiments herein.
Figure 15:
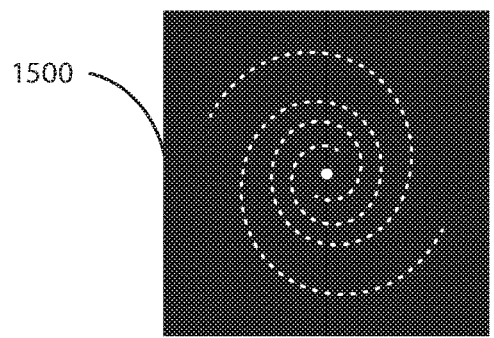
FIGS. 15-17 are schematic diagrams of additional configurations of light patterns formed by diffraction gratings in accordance with various embodiments herein.
Figure 16:
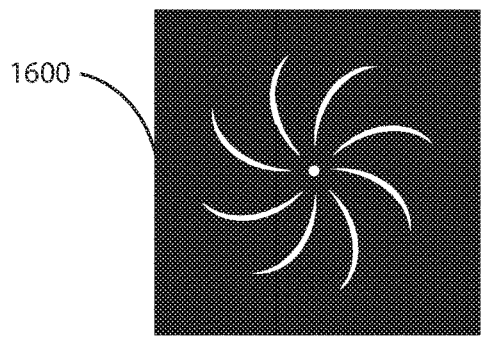
Figure 17:
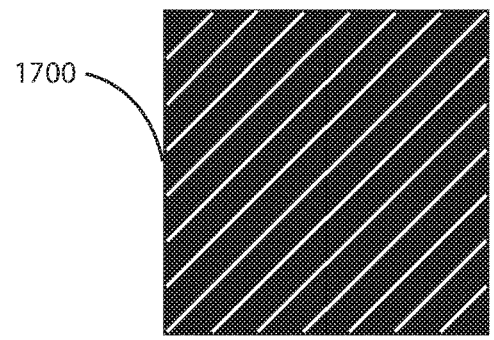

The photoacoustic catheters herein may include one or more diffraction gratings used to direct light from a light guide onto one or more specific locations on a surface of the balloon. Referring now to FIG. 13, a schematic cross-sectional view of a photoacoustic catheter 1300 is shown in accordance with various embodiments herein. The photoacoustic catheter 1300 includes a photoacoustic transducer 118 disposed about an outer surface of the balloon 122, where the balloon 122 can expand from a collapsed position to a first expanded configuration. The photoacoustic catheter 1300 includes an elongate shaft 102 and a first light guide 110 disposed along the elongate shaft 102. The first light guide 110 includes one or more diffraction grating patterns disposed along its length at a distal portion for directing or concentrating light 1302 from the first light guide 110 to one or more light pattern locations 1304 when the balloon 122 is in a first expanded configuration. The light pattern locations 1304 can include locations on balloon 122 or locations on the photoacoustic transducer 118. The light patterns formed by the diffraction gratings can selectively excite specific locations of the photoacoustic transducer 118 on a surface of the balloon.

The diffraction grating patterns can include, but are not to be limited to, the diffraction grating patterns shown in FIGS. 14-17. The configuration of diffraction grating patterns 1400 in FIG. 14 includes a dot matrix pattern. The configuration of diffraction grating patterns 1500 in FIG. 15 includes a spiral pattern. The configuration of diffraction grating patterns 1600 in FIG. 16 includes a fan-shaped pattern. The configuration of diffraction grating patterns 1700 in FIG. 17 includes a diagonal bar pattern. While only four examples are shown in FIGS. 14-17, it will be appreciated that the diffraction gratings suitable for use herein can include many configurations, including, but not to be limited to, longitudinal bars, concentric circles, concentric squares, concentric triangles, stars, discs, undulating waves, grids of squares, grids of triangles, grids of ovals, and the like.

Figure 18:
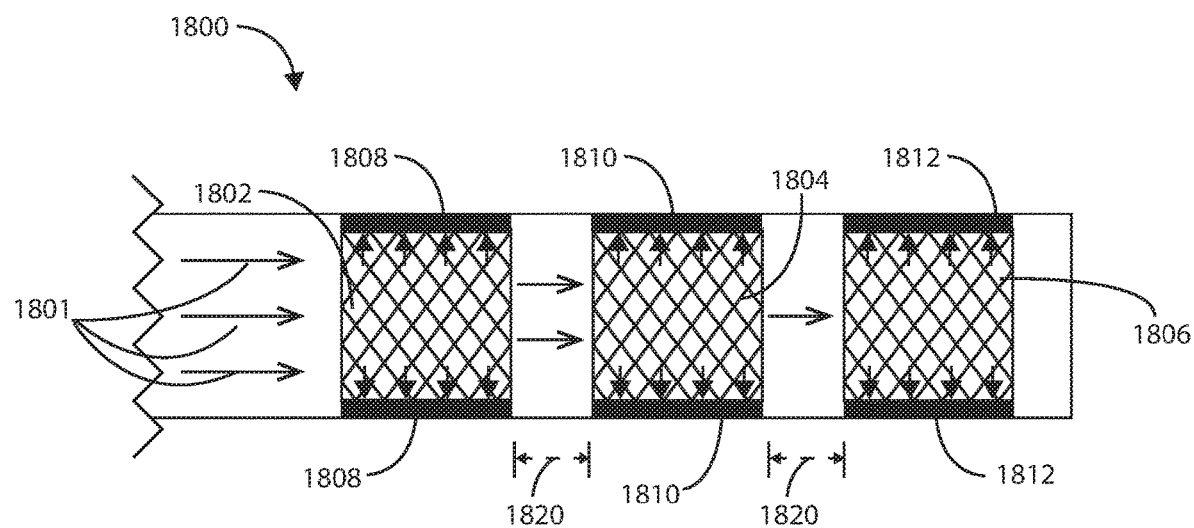
FIG. 18 is a schematic cross-sectional view of a light guide in accordance with various embodiments herein.

Light guides suitable for use in the embodiments herein can include one or more diffraction gratings and one or more fiber diffusers within the distal portion of the light guide to provide multiple selected regions within the light guide for directing toward the balloon surface. A fiber diffuser can be included as a part of the light guide that diverts light away from its axial path through the light guide and to a side surface portion. In some embodiments, the fiber diffusers can be included within the light guide at one or more regions of the distal portion. Referring now to FIG. 18 a schematic cross-sectional view of light guide 1800 is shown in accordance with various embodiments herein. Light guide 1800 includes a plurality of fiber diffusers including a first, second, and third fiber diffusers 1802, 1804, and 1806, respectively, positioned along the elongate shaft of the distal portion of the light guide 1800. Each fiber diffuser directs light 1801 from the light guide 1800 to exit the light guide 1800 at a side surface portion thereof. The side surface portions of the light guide 1800 are in optical communication with one or more diffraction gratings, such that the fiber diffusers and the diffraction gratings are in optical communication with one another.

By way of example, light guide 1800 includes a plurality of diffraction gratings including a first, second, and third diffraction gratings 1808, 1810, and 1812, respectively, positioned along the elongate shaft of the light guide 1800. The first, second, and third diffraction gratings 1808, 1810, and 1812, respectively, can be in optical communication with the first, second, and third fiber diffusers 1802, 1804, and 1806, respectively, at a plurality of side surface portions of light guide 1800. Light 1801 within each of the first, second, and third fiber diffusers 1802, 1804, and 1806 is directed to exit the light guide 1800 at a side surface portion and is dispersed by the first, second, and third diffraction gratings 1808, 1810, and 1812, respectively. Light energy can be dispersed by the diffraction gratings in a variety of ways depending on the configuration of the diffraction coating. The diffraction gratings 1808, 1810, and 1812 of light guide 1800 can be axially spaced apart with at least one intervening non-emitting portion 1820 of the light guide 1800 disposed between the plurality of diffraction gratings.

The fiber diffusers and diffraction gratings shown in FIG. 18 include those having a cylindrical shape. By way of example, the fiber diffusers 1802, 1804, and 1806 are configured to span the entire circumference of light guide 1800, and as such, the fiber diffusers 1802, 1804, and 1806 are cylindrical fiber diffusers. The diffraction gratings 1808, 1810, and 1812 are configured to span the entire circumference of light guide 1800, and as such, diffraction gratings 1808, 1810, and 1812 are cylindrical gratings.

Figure 19:
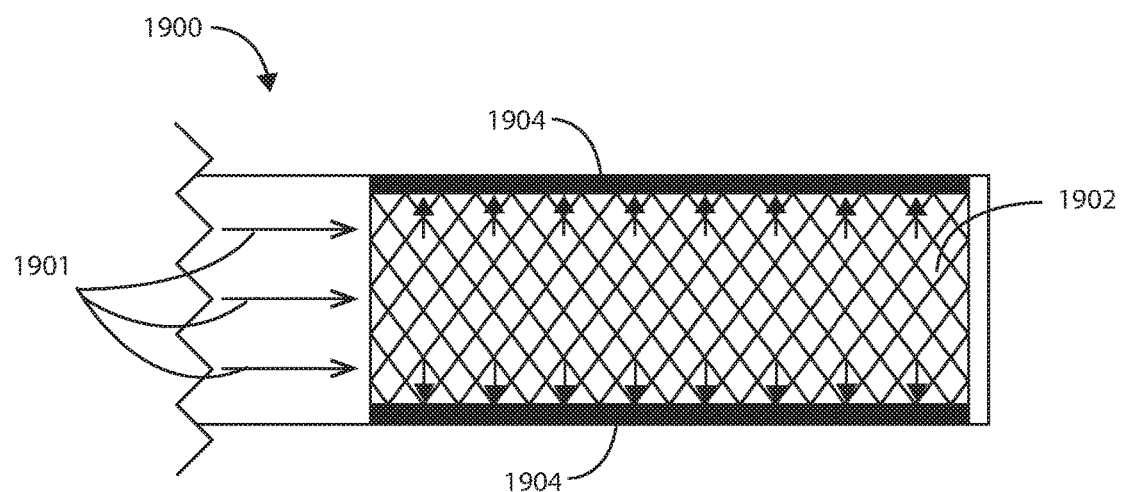
FIG. 19 is a schematic cross-sectional view of a light guide in accordance with various embodiments herein.

In some embodiments, a single large fiber diffuser can be included within the light guide at the distal portion. Referring now to FIG. 19 a schematic cross-sectional view of light guide 1900 is shown in accordance with various embodiments herein. Light guide 1900 includes a single fiber diffuser 1902 positioned along the elongate shaft of the distal region of the light guide 1900. The fiber diffuser 1902 directs light 1901 to exit the light guide 1900 at a side surface portion thereof. The side surface portion of the light guide 1900 is in optical communication with diffraction grating 1904 and fiber diffuser 1902, such that the fiber diffuser 1902 and the diffraction grating 1904 are in optical communication with one another.

Light 1901 is dispersed by the diffraction grating 1904 about the light guide 1900. The fiber diffuser 1902 and the diffraction grating 1904 can be configured to span the entire circumference of light guide 1900. The fiber diffuser 1902 can be a cylindrical fiber diffuser. The diffraction grating 1904 can be a cylindrical grating. The side surface portion of the light guide disposed in between the fiber diffuser 1902 and the diffraction grating 1904 can be a cylindrical side portion. While light guides 1800 and 1900 are shown having both fiber diffusers and diffraction gratings, it will be appreciated that in some embodiments the light guides herein can include only fiber diffusers. In some embodiments, the light guides herein can include those with only diffraction gratings. In other embodiments, the light guides herein can include those having any combination of fiber diffusers and diffraction gratings, or both.

To create diffraction gratings along the light guide, at least a portion of the cladding is removed or modified to provide an opening in the cladding that exposes a region of the light guide core for placement of a diffraction grating. In some embodiments, the portion of the cladding that is removed can be in the shape of a square, a circle, an oval, a trapezoid, and the like. In some embodiments, the portion of the cladding removed from the light guide can extend circumferentially about the entire light guide. In other embodiments, the portion of the cladding removed from the light guide can extend circumferentially about a portion of the light guide. In some embodiments, the diffraction grating is integral to a cladding layer about the light guide. In yet other embodiments, the portion of the cladding removed from the light guide can be in the shape of a spiral circumferentially disposed about a portion of the light guide.

Figure 20:
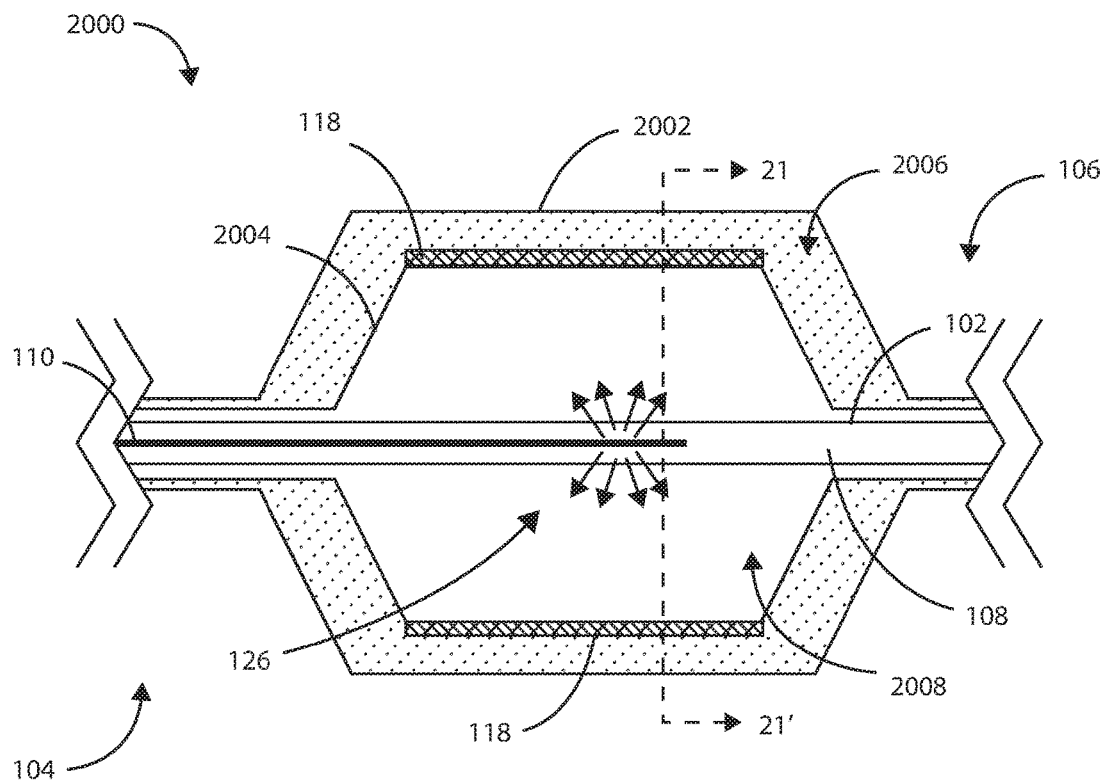
FIG. 20 is a schematic cross-sectional view of a photoacoustic catheter in accordance with various embodiments herein.

It will be appreciated that the photoacoustic catheters herein can include multiple balloons. Referring now to FIG. 20, a schematic cross-sectional view of a photoacoustic catheter 2000 is shown in accordance with various embodiments herein. Photoacoustic catheter 2000 can be adapted for placement within a blood vessel having a vessel wall. The photoacoustic catheter 2000 can be used to treat a vascular lesion found within or adjacent to the vessel wall. In some embodiments, the vascular lesion can include a calcified vascular lesion. In some embodiments, the vascular lesion can include a fibrous vascular lesion. The photoacoustic catheter 2000 can include an elongate shaft 102 extending from a proximal region 104 to a distal region 106, and can also include a lumen 108. In some embodiments, the photoacoustic catheter 2000 can have a distal region opening and can accommodate and be tracked over a guide wire to a treatment location. In some embodiments, the photoacoustic catheter 2000 does not include a lumen. In embodiments where the elongate shaft 102 does not include a lumen to be accessed by a caregiver, the elongate shaft 102 can be configured to allow the catheter to be steered through a patient's vasculature. For example, a wire extension at a distal region of the elongate shaft can improve steerability.

The elongate shaft 102 of photoacoustic catheter 2000 can be coupled to a first light guide 110 in optical communication with a light source 116. In some embodiments, the first light guide can be an optical fiber and the light source can be a laser. The light source 116 can be in optical communication with the first light guide 110 at a proximal region 104 of the elongate shaft 102. A schematic depiction of exemplary emitted light 126 as transmitted by the first light guide 110 is shown. It will be appreciated that, photoacoustic catheter 2000 can include more than one light guide. In some embodiments, photoacoustic catheter 2000 can include a second light guide, a third light guide, a fourth light guide, a fifth light guide, a sixth light guide, or more. In some embodiments, a plurality of light guides will be evenly spaced and radially offset from each other so that where there are n light guides, they are spaced apart by 360 degrees divided by n. In other embodiments, the light guides will be unevenly spaced and radially offset from each other.

It will be appreciated that the photoacoustic catheters herein can include any number of light guides. For example, in some embodiments, the photoacoustic catheters herein can include from one light guide to five light guides. In other embodiments, the photoacoustic catheters herein can include from five to fifteen light guides. In yet other embodiments, the photoacoustic catheters herein can include from ten light guides to thirty light guides. The photoacoustic catheters herein can include one, two, three, four, five, six, seven, eight, nine, or ten light guides. The photoacoustic catheters can include 11, 12, 13, 14, 15, 16, 17, 18, 19, 20, 21, 22, 23, 24, 25, 26, 27, 28, 29, or 30 light guides. It will be appreciated that photoacoustic catheters herein can include any number of light guides that can fall within a range, wherein any of the forgoing numbers can serve as the lower or upper bound of the range, provided that the lower bound of the range is a value less than the upper bound of the range. In some embodiments, the photoacoustic catheters herein can include more than 30 light guides.

The photoacoustic catheter 2000 includes an outer balloon 2002 coupled to the elongate shaft 102. The outer balloon 2002 can expand from a collapsed configuration 2302 (illustrated in FIG. 23) suitable for advancing the catheter through a patient's vasculature to a first expanded configuration 2304 (illustrated in FIG. 23) suitable for anchoring the catheter in position relative to a treatment site. The photoacoustic catheter 2000 also includes an inner balloon 2004 coupled to the elongate shaft 102. The inner balloon 2004 can expand from a collapsed configuration suitable for advancing the catheter through a patient's vasculature to a first expanded configuration. In some embodiments, the outer balloon 2002 and/or inner balloon 2004 are configured to change from a first expanded configuration to a second, further expanded configuration. It will be appreciated that the balloons herein can assume multiple expanded configurations between a first expanded configuration and a second further expanded configuration. In some embodiments, the balloons herein will include a maximum expanded configuration. Expansion of the balloons herein to various expanded configurations will be discussed in more detail below.

The inner balloon 2004 of photoacoustic catheter 2000 can include a photoacoustic transducer 118 disposed on a surface of the inner balloon 2004 and can be in optical communication with the first light guide 110. In some embodiments, the photoacoustic transducer 118 is disposed on an outer surface of the inner balloon 2004, as shown in FIG. 20. In other embodiments, the photoacoustic transducer 118 is disposed on an inner surface of the inner balloon 2004, as discussed in reference to FIG. 3.

The photoacoustic transducer 118 disposed on the inner balloon 2004 can be adapted to impart acoustic pressure waves upon a calcified lesion to induce fractures in the calcified lesion. The photoacoustic transducer 118 can be formed from a light-absorbing material and a thermal expansion material. In some embodiments, the thermal expansion material of the photoacoustic transducer 118 is a polymer, and the polymer is in thermal contact with the light absorbing material. The thermal expansion material and the light absorbing material will both be discussed in more detail below.

The photoacoustic catheter 2000 can be configured to expand the outer balloon 2002 using an outer balloon inflation fluid 2006 and configured to expand the inner balloon 2004 using an inner balloon inflation fluid 2008. The balloon inflation fluids herein can include a fluid suitable for transmitting acoustic energy from the first light guide 110 to an inside surface of the outer balloon 2002 and the inner balloon 2004. Exemplary balloon inflation fluids can include, but are not to be limited to, water, saline, contrast agent, gases such as oxygen and carbon dioxide, and the like, and will be discussed in more detail below. In some embodiments, the outer balloon inflation fluid 2006 is a liquid and the inner balloon inflation fluid 2008 is a gas. In some embodiments, the outer balloon inflation fluid 2006 is a gas and the inner balloon inflation fluid 2008 is a liquid. In some embodiments the inner balloon inflation fluid 2008 is the same as the outer balloon inflation fluid 2006. In some embodiments, an acoustic impedance mismatch can exist between inner balloon inflation fluid 2008 and outer balloon inflation fluid 2006 to increase acoustic coupling efficiency.

Figures 21, 22:
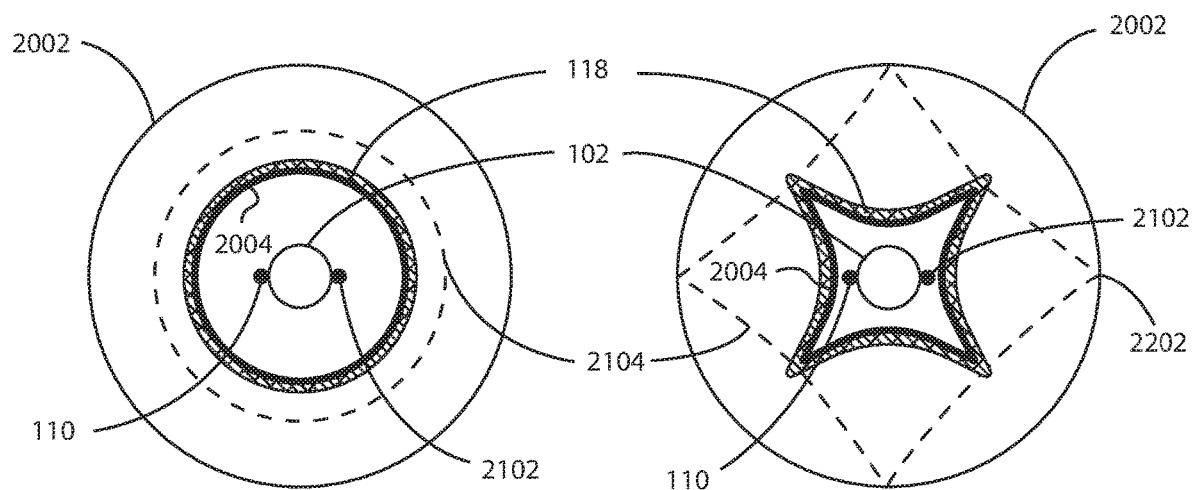
FIG. 21 is a schematic cross-sectional view of the photoacoustic catheter of FIG. 20 along line 21-21' in accordance with various embodiments herein.
FIG. 22 is a schematic cross-sectional view of an additional configuration of the photoacoustic catheter of FIG. 20 along line 21-21' in accordance with various embodiments herein.

Referring now to FIGS. 21 and 22, cross-sectional views of photoacoustic catheter 2000 along line 21-21' of FIG. 20 are shown in accordance with various embodiments herein. The photoacoustic catheter 2000 includes the outer balloon 2002, the inner balloon 2004, elongate shaft 102, a first light guide 110, a second light guide 2102, and a photoacoustic transducer 118 disposed about the outer surface of the inner balloon 2004. In some embodiments, the photoacoustic transducer 118 can be disposed about the inner surface of inner balloon 2004.

The cross-sectional view presented in FIG. 21 shows an inner balloon 2004 with a symmetrical shape and photoacoustic transducer 118 when in a first expanded configuration. The photoacoustic transducer 118 can be activated by a light source 116 in optical communication with the first light guide 110, the second light guide 2102, and the photoacoustic transducer 118 to generate at least one acoustic pressure wave 2104. The cross-sectional view presented in FIG. 22 shows an inner balloon 2004 with an asymmetrical shape and photoacoustic transducer 118 having a concave portion in a first expanded configuration. The photoacoustic transducer 118 can be activated by a light source 116 in optical communication with the first light guide 110, the second light guide 2102, and the photoacoustic transducer 118 to generate at least one acoustic pressure wave 2104 having at least one focal point 2202 on an inner surface of the outer balloon 2002. While the embodiments shown in FIGS. 21 and 22 include only a first light guide and a second light guide, it will be appreciated that multiple light guides can be used in photoacoustic catheter 2000, as discussed elsewhere herein.

It will be appreciated that the configuration of inner balloon 2004 of FIG. 22 can be further used to focus light to a specific location along a vascular lesion. While the configuration of FIG. 22 shows four concave portions for inner balloon 2004, it will be appreciated that the inner balloon can be configured to include from two to ten focusing elements disposed about the elongate shaft. In some embodiments, the inner balloon can be configured to include more than ten focusing elements about the elongate shaft. The focusing elements can be disposed uniformly or non-uniformly about the elongate shaft depending on the shape, size, and location of the vascular lesion to be treated. For example, for circumferential lesions, the inner balloon 2004 could include from two to ten focusing elements distributed evenly about the elongate shaft. For non-circumferential lesions, the inner balloon 2004 could include from two to ten focusing elements distributed non-uniformly about the elongate shaft. The acoustic focusing elements suitable for use herein can include a hydrophobic coating on the surface of the balloon, a honeycomb-like structure filled with gas or gas bubbles, a concave balloon-shaping structure made from nitinol, magnesium alloys, titanium alloys, biocompatible polymers, and the like. It will be further appreciated that the focusing elements of FIG. 22 can be present on a single balloon without an additional outer balloon present.

Methods

Figure 23:
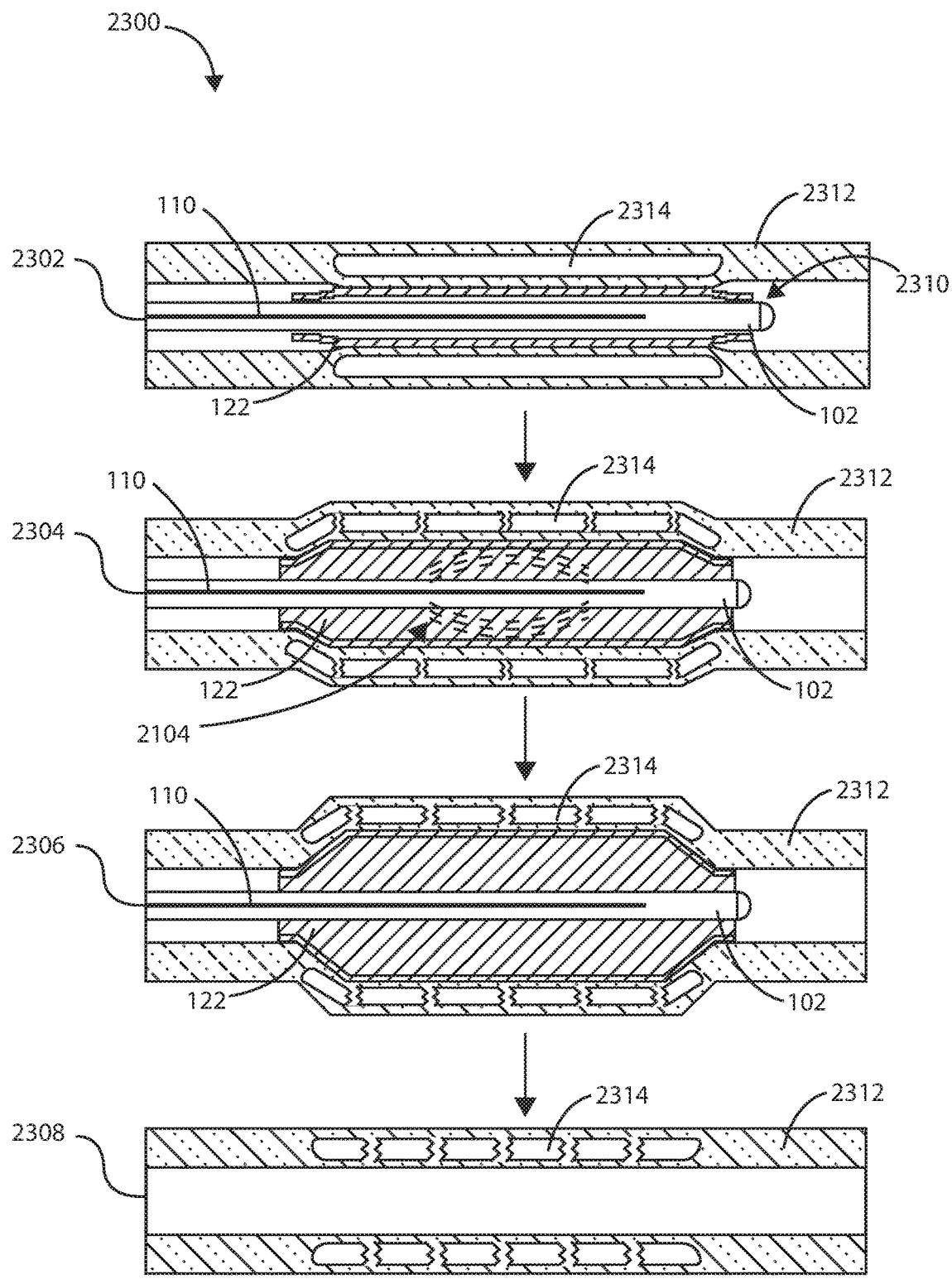
FIG. 23 is a schematic flow diagram for a method in accordance with the various embodiments herein.

The photoacoustic catheters described herein can be used in one or more methods for photoacoustically generating pressure waves within a blood vessel. Referring now to FIG. 23, a schematic flow diagram for a method 2300 is shown in accordance with the various embodiments herein. Method 2300 includes advancing a photoacoustic catheter 2310 to a treatment site 2314 within the blood vessel 2312, the photoacoustic catheter 2310 including an elongate shaft 102, a balloon 122 coupled to the elongate shaft 102, a first light guide 110, and a photoacoustic transducer 118 (not shown) disposed on a surface of the balloon 122 at 2302. The treatment site 2314 can include a vascular lesion within a patient's vasculature. In some embodiments, the vascular lesion can include a calcified lesion. In some embodiments, the vascular lesion can include a fibrous vascular lesion. The method 2300 includes expanding the balloon 122 from a collapsed configuration suitable for advancing the catheter through a patient's vasculature to a first expanded configuration 2304 suitable for anchoring the catheter in position relative to the treatment site 2314 at 2304. The method 2300 includes, after expanding the balloon 122, activating a light source 116 in optical communication with the first light guide 110 and the photoacoustic transducer 118, thereby imparting acoustic pressure waves 2104 upon the treatment site 2314 at 2304. The method 2300 can also include, after activating the light source, further expanding the balloon 122 from the first expanded configuration 2304 to a second further expanded configuration at 2306. The method can include completely removing the photoacoustic catheter 2310 from the patient's vasculature at 2308.

Balloons

The balloons suitable for use in the photoacoustic catheters herein include those that exhibit good adhesion to the photoacoustic transducer materials described herein. For embodiments where the photoacoustic transducer is disposed on the exterior surface of the balloon, suitable balloon materials exhibit a high transparency for light. Without being bound by any particular theory, transparency can refer to the ability of a material to transmit light without appreciable scattering of the light by the material and is reported as total transmittance. Transmittance is reported as the ratio of transmitted light to the incident light, and can be reduced by reflection of light by the material, scattering of light by the material, and absorption of light by the material. In some embodiments, the materials suitable for use in the balloons herein can include those with a transmittance of about 50% to about 100%. In some embodiments, the transmittance can be greater than or equal to 50%, 60%, 70%, 80%, 90%, or 100%, or can be an amount falling within a range between any of the foregoing.

The balloons herein can be configured to be expanded from a collapsed configuration suitable for advancing the catheter through a patient's vasculature to a first expanded configuration suitable for anchoring the catheter in position relative to a treatment site. After treatment at a treatment site, the balloon can be further expanded from the first expanded configuration to a second further expanded configuration. In some embodiments, the second further expanded configuration includes a balloon diameter larger than the balloon diameter of the first expanded configuration. It will be appreciated that the balloons herein can assume multiple expanded configurations between the first expanded configuration and a second further expanded configuration. In some embodiments, the balloons herein will include a maximum expanded configuration. In some embodiments, the second further expanded configuration can be the maximum expanded configuration of the balloon.

In some embodiments, the balloons herein are made from silicone. In other embodiments, the balloons herein are made from polydimethylsiloxane (PDMS), polyurethane, polymers such as PEBAX™ material available from Arkema (which has a location at King of Prussia, Pa., USA), nylon, and the like. In some embodiments, the balloons can include those having diameters ranging from 1 millimeter (mm) to 25 mm in diameter. In some embodiments, the balloons can include those having diameters ranging from 1.5 mm to 12 mm in diameter. In some embodiments, the balloons can include those having diameters ranging from 1 mm to 5 mm in diameter. In some embodiments, the diameter can be greater than or equal to 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, or 20.0 mm, or can be an amount falling within a range between any of the foregoing.

In some embodiments, the balloons herein can include those having a length ranging from 5 mm to 300 mm in length. In some embodiments, the balloons herein can include those having a length ranging from 8 mm to 200 mm in length. In some embodiments, the length of the balloon can be greater than or equal to 5 mm, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or can be an amount falling within a range between any of the foregoing.

The balloons herein can be inflated to inflation pressures from 1 atmosphere (atm) to 70 atm. In some embodiments, the balloons herein can be inflated to inflation pressures of from 6 atm to 20 atm. In some embodiments, the balloons herein can be inflated to inflation pressures of from 20 atm to 70 atm. In some embodiments, the balloons herein can be inflated to inflation pressures that can be greater than or equal to 1 atm, 10 atm, 20 atm, 30 atm, 40 atm, 50 atm, 60 atm, or 70 atm, or can be an amount falling within a range between any of the foregoing.

The balloons herein can include those having various shapes, including, but not to be limited to, a conical shape, a square shape, a rectangular shape, a spherical shape, a conical/square shape, a conical/spherical shape, an extended spherical shape, an oval shape, a tapered, shape, a bone shape, a stepped diameter shape, an offset shape, or a conical offset shape.

In some embodiments, the balloons herein can provide a therapeutic agent to a treatment site. In some embodiments, the therapeutic agent can be delivered via a drug eluting coating, a drug eluting stent structure, or by the delivery of a drug composition through one or more lumens of the catheters described herein. The drug elution coating or drug eluting stent structure can include one or more therapeutic agents including anti-inflammatory agents, anti-neoplastic agents, anti-angiogenic agents, and the like. Exemplary agents can include, but is not to be limited to paclitaxel, docetaxel, everolimus, and sirolimus, and analogs thereof.

Figure 24:
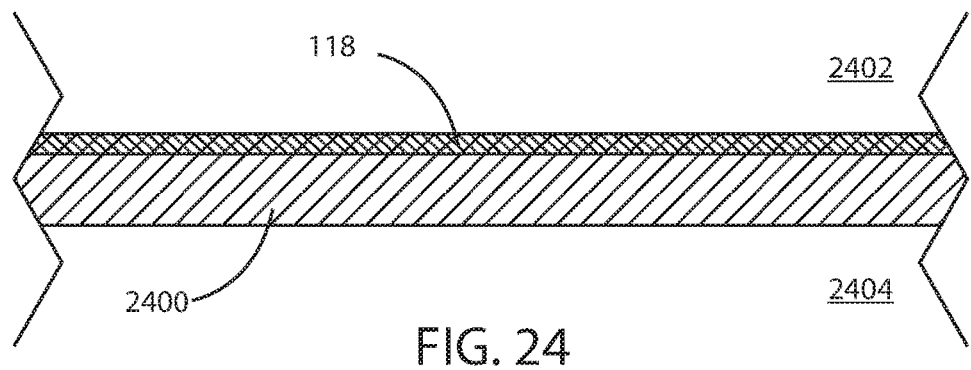
FIG. 24 is a schematic cross-sectional view of a portion of a photoacoustic catheter in accordance with various embodiments herein.
Figure 25:
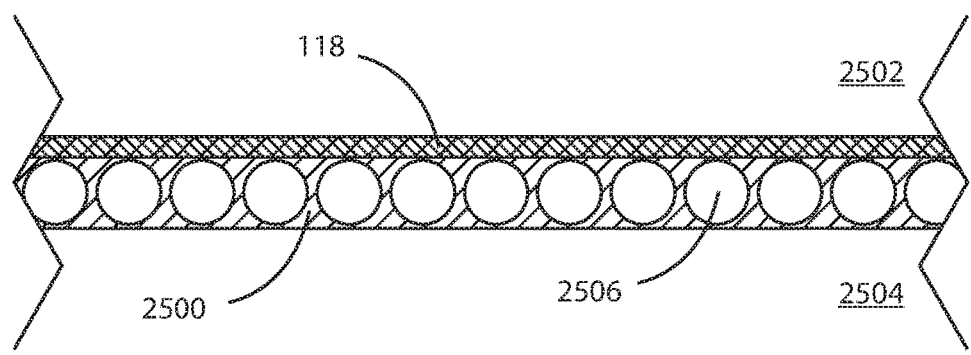
FIG. 25 is a schematic cross-sectional view of a portion of a photoacoustic catheter in accordance with various embodiments herein.

The balloons suitable for use in the photoacoustic catheters herein can include one or more acoustic focusing elements, such as an acoustic mirror. Referring now to FIGS. 24-25, schematic cross-sectional views of a balloon are shown in accordance with various embodiments herein. In the configuration shown in FIG. 24, a balloon 2400 includes an outer surface 2402 that can be exposed to the luminal wall of a vessel within a patient and an inner surface 2404 that is disposed on the interior of the balloon 2400. Balloon 2400 includes a photoacoustic transducer 118 disposed on an outer surface of a balloon 2400. The balloon 2400 does not include an acoustic focusing element. In the configuration shown in FIG. 25, a balloon 2500 includes an outer surface 2502 that can be exposed to the luminal wall of a vessel within a patient and an inner surface 2504 that is disposed on the interior of the balloon 2500. Balloon 2500 includes a photoacoustic transducer 118 disposed on an outer surface of the balloon 2500, and further includes a plurality of gas bubbles 2506 integrated within the balloon material of balloon 2500. The plurality of gas bubbles 2506 can act as an acoustic focusing element, such as an acoustic mirror, used to focus the acoustic pressure wave at any given location(s) on the vessel wall of a patient to treat a vascular lesion.

Figure 26:
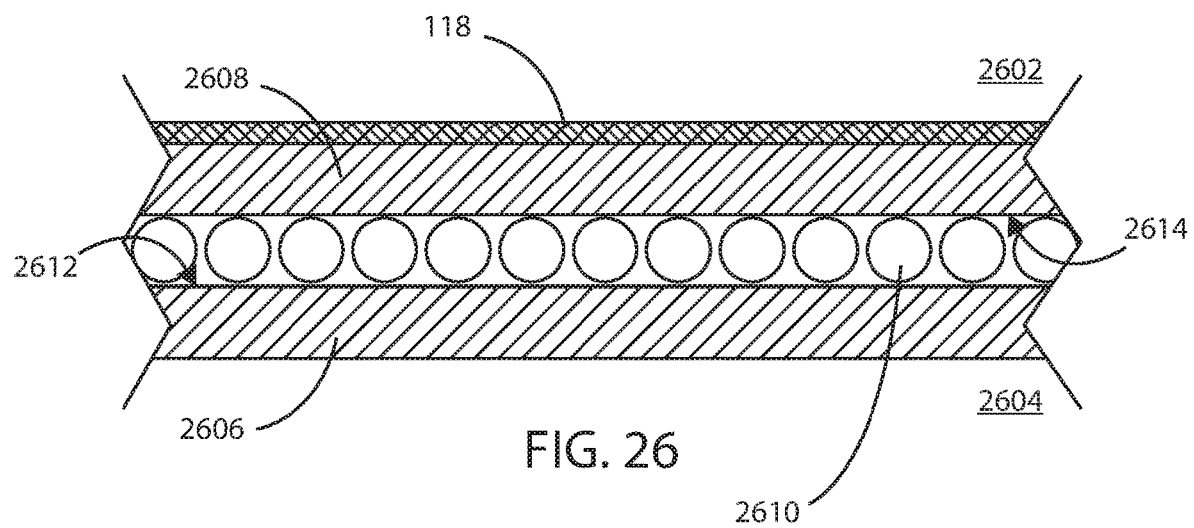
FIG. 26 is a schematic cross-sectional view of a portion of a photoacoustic catheter in accordance with various embodiments herein.

Embodiments herein having multiple balloons can also be configured to include one or more focusing elements. By way of example, two balloon walls can be configured to trap gas therebetween such that the trapped gas can act as an acoustic mirror. In the configuration shown in FIG. 26, the photoacoustic catheter can include an inner balloon 2606 and an outer balloon 2608. The outer balloon 2608 can include an outer surface 2602 that can be exposed to the luminal wall of a vessel within a patient and an inner surface 2614 facing the inner balloon 2606. The inner balloon 2606 can include an inner surface 2604 that is disposed on an interior portion of the photoacoustic catheter and exposed to a balloon fluid, and an outer surface 2612 facing the outer balloon 2608. The outer balloon 2608 can include a photoacoustic transducer 118 disposed on the outer surface of the outer balloon 2608. The inner balloon 2606 and the outer balloon 2608 can be configured to trap a plurality of gas bubbles 2610 in between the inner surface 2614 of outer balloon 2608 and the outer surface 2612 of inner balloon 2606 when in an expanded configuration. In one example, the outer balloon 2608 has smooth surfaces on both the outer surface 2602 and inner surface 2614, while the inner balloon 2606 has a smooth inner surface 2604 and features or structures on the outer surface 2612 so that when inflated against the outer balloon, gas is trapped in the features or structures to create an acoustic mirror. The plurality of gas bubbles 2610 trapped between the inner balloon 2606 and outer balloon 2608 can act as an acoustic focusing element used to focus the acoustic pressure wave at any given location(s) on the vessel wall of a patient to treat a vascular lesion. The acoustic focusing elements suitable for use on a surface of the inner balloon 2606 or outer balloon 2608 can further include a hydrophobic coating a honeycomb-like structure filled with gas or gas bubbles, a concave balloon-shaping structure made from nitinol, magnesium alloys, titanium alloys, biocompatible polymers, and the like.

Balloon Fluids

Exemplary balloon fluids suitable for use herein can include, but are not to be limited to one or more of water, saline, contrast agent, fluorocarbons, perfluorocarbons, gases, such as carbon dioxide, and the like. In some embodiments, the balloon inflation fluids include a mixture of saline to contrast agent in a volume ratio of 50:50. In some embodiments, the balloon fluids include a mixture of saline to contrast agent in a volume ratio of 25:75. In some embodiments, the balloon fluids include a mixture of saline to contrast agent in a volume ratio of 75:25. The balloon fluids suitable for use herein can be tailored on the basis of composition, viscosity, and the like in order to manipulate the rate of travel of the acoustic pressure waves therein. The balloon fluids suitable for use herein are biocompatible.

In some embodiments, the contrast agents used herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12), perfluoro-octane (PFO), perfluoroperhydrophenanthrene, perfluorodecalin (PFD), perfluorotributylamide (PFTB) and perfluorooctylbromide (PFOB), and the like.

Photoacoustic Transducers

The photoacoustic transducers herein can include those that can be disposed on the internal surface of a balloon or the external surface of a balloon. The photoacoustic transducers disposed on a surface of the balloon can include those that are configured to span the entire circumference of balloon. In some embodiments, the photoacoustic transducers can also include partial transducers that are configured to span from at least 1 to 359 degrees about the balloon in a circumferential direction. In some embodiments, the photoacoustic transducers herein can be disposed on a surface of the balloon in one or more photoacoustic transducer patterns as described herein. By way of example, the photoacoustic transducer patterns can include, but are not to be limited to, circumferential bars, longitudinal bars, diagonal bars, or islands of various shapes and sizes. In various embodiments herein, the photoacoustic catheters can include a plurality of photoacoustic transducers, including a first photoacoustic transducer, a second photoacoustic transducer, a third photoacoustic transducer, a fourth photoacoustic transducer, a fifth photoacoustic transducer, a sixth photoacoustic transducer, a seventh photoacoustic transducer, an eighth photoacoustic transducer, a ninth photoacoustic transducer, a tenth photoacoustic transducer, etc.

Without wishing to be bound by any particular theory, the photoacoustic transducer patterns having multiple photoacoustic transducers herein can be tailored to generate acoustic pressure waves such that adjacent photoacoustic transducers generate acoustic pressure waves that can constructively interfere with one another to generate higher peak pressure at a given location within the vascular lesion.

The photoacoustic transducers herein can generate acoustic pressure waves upon the site of a calcified lesion. The acoustic pressure waves generated by the photoacoustic transducers can be tailored for the specific application, including directionality, shape, convergence, or divergence by tailoring the size, shape and excitation of the photoacoustic transducer(s) and the balloon surface. In some embodiments, the photoacoustic transducer(s) and balloon surface can be tailored to generate a cylindrical acoustic wave symmetrically about a balloon. In other embodiments, the photoacoustic transducers can be tailored to generate multiple acoustic pressure waves from more than one location on a surface of a balloon. In other embodiments, the photoacoustic transducers can be tailored to generate multiple acoustic pressure waves that are directionally offset from one another by from zero degrees to 180 degrees about the balloon.

The size of the photoacoustic transducers can vary and can depend on the treatment location to be accessed. In some embodiments, the photoacoustic transducers can be from 0.1 mm to 6 mm, 0.1 mm to 2 mm, or 10 mm to 100 mm in diameter or width. In some embodiments, the photoacoustic transducers can be from 5 mm to 30 mm in diameter or width. In some embodiments, the photoacoustic transducers can be from 10 mm to 20 mm in diameter or width. A size for a single photoacoustic transducer of about 1 $mm^2$ or less is possible and has efficiency advantages over larger photoacoustic transducers. In other embodiments, the photoacoustic transducers can collectively span from 0.1 mm to 6 mm, 0.1 mm to 2 mm, 10 mm to 100 mm, from 5 mm to 30 mm along the length of the balloon. In yet other embodiments, the photoacoustic transducers can exceed 30 mm in length, exceed 100 mm in length, such as in the context of coronary treatment, or exceed 200 mm to 300 mm in length, such as in the context of peripheral vascular treatment.

The photoacoustic transducers herein can include a light-absorbing material and a thermal expansion material. Exemplary light absorbing material suitable for use herein can include strong light-absorbing materials having large absorption coefficients of units inverse centimeters. Some exemplary light-absorbing materials can include, but not be limited to, nanoparticles, carbon nanotubes, candle soot, candle soot nanoparticles, carbon black, a nanotube array, multiwall carbon nanotubes, and light absorbing dyes. The light-absorbing materials herein can be highly absorbing of laser light such that absorption is rapid on the nanosecond timescale. The rapid absorption of light energy by the light-absorbing material can enable the efficient transfer of thermal energy to the thermal expansion material, thus driving the generation of acoustic waves.

Thermal expansion materials suitable for use herein can include materials having a strong coefficient of thermal expansion. For example, the thermal expansion material can have a coefficient of thermal expansion from 23 degrees Celsius to 100 degrees Celsius of about 0.000012 1/K or higher, about 0.0001 1/K or higher, 0.0002 1/K or higher, or about 0.0003 1/K or higher.

Suitable thermal expansion materials can include polymers having a strong coefficient of thermal expansion. Examples of suitable materials include, but are not to be limited to, polydimethylsiloxane (PDMS), polytetrafluoroethylene (PTFE), polyimide, polyisobutylene (FIB), PIB polyurethane, polyurethanes, styrene isoprene butadiene, ethylene propylene polyacrylic, ethylene acrylic, fluorosilicone, polybutadiene, polyisoprene, and thermoplastic elastomers. For a silicone PDMS material, the coefficient of thermal expansion from 23 degrees Celsius to 100 degrees Celsius can be about 0.00034 1/K. For a plain PTFE material, the coefficient of thermal expansion from 23 degrees Celsius to 100 degrees Celsius can be about 0.000143 1/K. For a polyimide material, the coefficient of thermal expansion from 23 degrees Celsius to 100 degrees Celsius can be about 0.00014 1/K.

Thermal expansion materials suitable for use herein can also include thin metallic films. Thin metallic films can be used alone, or in combination with additional thermal expansion materials, such as thermal expansion materials having a high coefficient of thermal expansion (CTE). Some exemplary metals for use as thermal expansion materials in thin metallic films include, but are not to be limited to silver, copper, and gold, aluminum, beryllium, tungsten, and magnesium.

The photoacoustic transducers herein can be formed by layering a light-absorbing material and a thermal expansion material on a surface of the balloons described herein. In some embodiments, the light-absorbing material and a thermal expansion material can form a composite film on or around the balloons described herein. In some embodiments, the composite film can include one that has layers of the light-absorbing material. In one embodiment, a layer of the light-absorbing material can be disposed on a balloon in optical contact with the core of the light guide and a thermal expansion material can be disposed on the surface of the light-absorbing material layer at the outermost surface. In some embodiments, the thermal expansion material is in thermal contact with the light absorbing material. In some embodiments, the thermal expansion material is in direct contact with the light absorbing material. In other embodiments, the thermal expansion material is in a matrix with the light absorbing material. In yet other embodiments, the thermal expansion material and the light absorbing material are the same.

One suitable configuration for the light-absorbing material and a thermal expansion material can include a layer of candle-soot nanoparticles as the light-absorbing material in contact with a layer of polydimethylsiloxane as the thermal expansion material. Another suitable configuration for the light-absorbing material and a thermal expansion material can include a layer of multiwall carbon nanotubes as the light-absorbing material in contact with a layer of polydimethylsiloxane as the thermal expansion material.

The light-absorbing material and a thermal expansion material can be applied to the balloons using various techniques. In some embodiments, the light-absorbing material and a thermal expansion material can be individually applied to the balloons using a spray coating technique. In other embodiments, the light-absorbing material and a thermal expansion material can be individually applied to the balloons using a dip coating technique. In yet other embodiments, the light-absorbing material and a thermal expansion material can be individually applied to the balloons using an e-spun coating technique.

Light Guides (FIGS. 27-30 and 43-45)

The light guides herein can include an optical fiber or flexible light pipe. The light guides herein can be thin and flexible and can allow light signals to be sent with very little loss of strength. The light guides herein can include a core surrounded by a cladding about its circumference. In some embodiments, the core can be a cylindrical core or a partially cylindrical core. The core and cladding of the light guides can be formed from one or more materials, including but not limited to one or more types of glass, silica, or one or more polymers. The light guides may also include a protective coating, such as a polymer. It will be appreciated that the index of refraction of the core will be greater than the index of refraction of the cladding.

Each light guide can guide light along its length to a distal portion having a photoacoustic transducer connected thereto. The light guide can create a light path as a portion of an optical network including a light source. The light path within the optical network allows light to travel from one part of the network to another without being modified. Both the optical fiber or the flexible light pipe can provide a light path within the optical networks herein.

The light guides herein can assume many configurations about the elongate shaft of the photoacoustic catheters described herein. In some embodiments, the light guides can run parallel to the longitudinal axis of the elongate shaft of the photoacoustic catheter. In some embodiments, the light guides can be disposed spirally or helically about the longitudinal axis of the elongate shaft of the photoacoustic catheter. In some embodiments, the light guides can be physically coupled to the elongate shaft. In other embodiments, the light guides can be disposed along the length of the outer diameter of the elongate shaft. In yet other embodiments the light guides herein can be disposed within one or more light guide lumens within the elongate shaft. Various configurations for the elongate shafts and light guide lumens will be discussed below.

Figure 27:
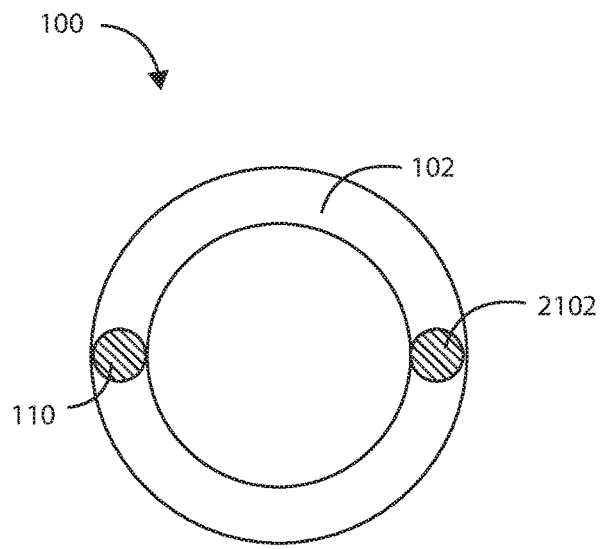
FIG. 27 is a schematic cross-sectional view of an elongate shaft and multiple light guides of a photoacoustic catheter along line 27-27' in FIG. 1 in accordance with various embodiments herein.
Figure 28:
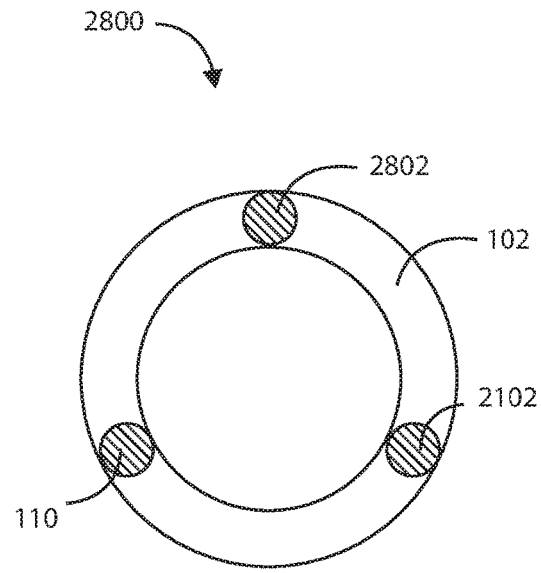
FIGS. 28-30 are schematic cross-sectional views of additional configurations for an elongate shaft and multiple light guides of a photoacoustic catheter along line 27-27' in FIG. 1 in accordance with various embodiments herein.
Figure 29:
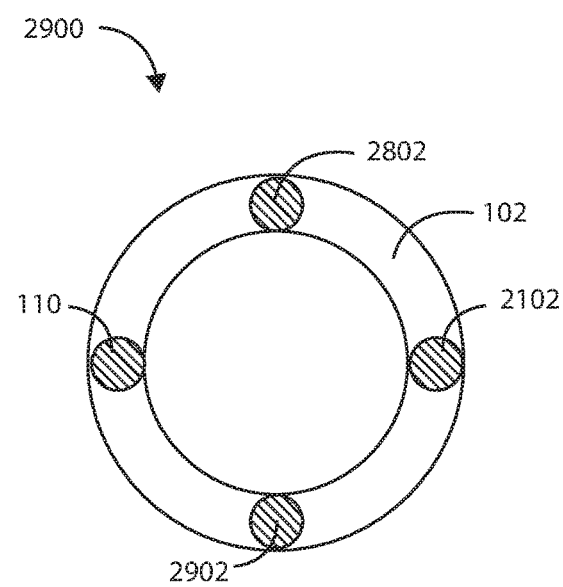
Figure 30:
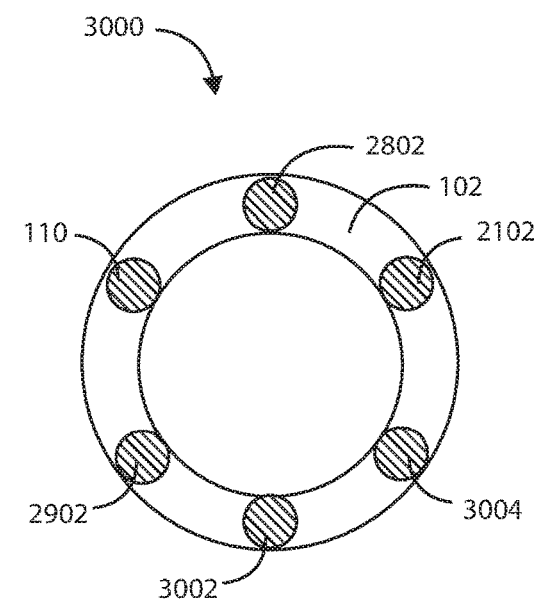
Figure 33:
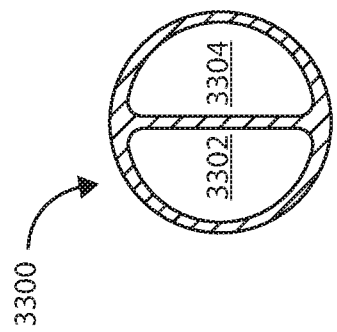
FIGS. 31-42 are schematic cross-sectional views of additional embodiments of an elongate shaft of a photoacoustic catheter in accordance with various embodiments herein.
Figure 36:
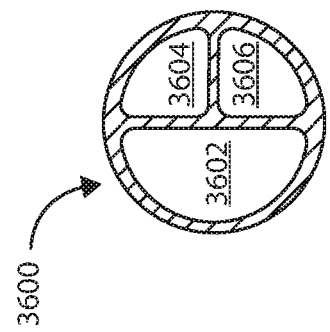
Figure 32:
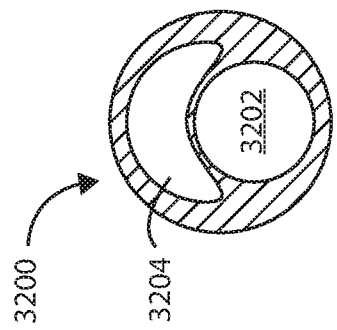
Figure 35:
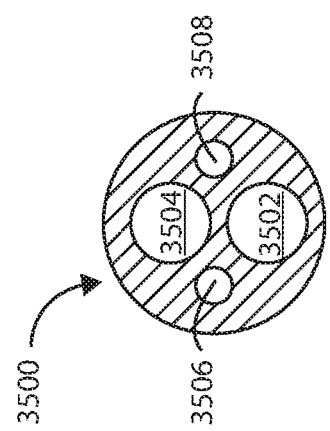

Examples of photoacoustic catheters having multiple light guides disposed about the elongate shaft at different positions around the circumference are shown in FIGS. 27-30. Referring now to FIG. 27, a schematic cross-sectional view of a photoacoustic catheter 100 of FIG. 1 along line 27-27' in FIG. 1 is shown in accordance with various embodiments herein. Photoacoustic catheter 100 includes an elongate shaft 102, a first light guide 110 and a second light guide 2102 separated by about 180 degrees around the circumference. Referring now to FIGS. 28-30, schematic cross-sectional views of additional configurations for photoacoustic catheters having multiple light guides are shown in accordance with various embodiments herein. The configuration of photoacoustic catheter 2800 in FIG. 28 includes an elongate shaft 102, a first light guide 110, a second light guide 2102, and a third light guide 2802 separated by about 120 degrees around the circumference. The configuration of photoacoustic catheter 2900 in FIG. 29 includes an elongate shaft 102, a first light guide 110, a second light guide 2102, a third light guide 2802, and a fourth light guide 2902 separated by about 90 degrees around the circumference. The configuration of photoacoustic catheter 3000 shown in FIG. 30 includes an elongate shaft 102, a first light guide 110, a second light guide 2102, a third light guide 2802, a fourth light guide 2902, a fifth light guide 3002, and a sixth light guide 3004 separated by about 60 degrees around the circumference.

When multiple light guides are present, the light guides can be radially offset from one another by about at least about or about 45 degrees. In some embodiments, the light guides can be radially offset from one another by at least about or about 60 degrees. In some embodiments, the light guides can be radially offset from one another by about at least about or 90 degrees. In some embodiments, the light guides can be radially offset from one another by about 180 degrees. In some embodiments, a plurality of light guides will be evenly spaced and radially offset from each other so that where there are n light guides, they are spaced apart by 360 degrees divided by n. In some embodiments, each of the light guide locations shown in FIGS. 27-30 or otherwise described herein include two parallel light guides that are touching.

The light guides herein can include one or more diverting features configured to direct light within the light guide toward a side surface portion of the distal portion of the light guide. The diverting feature can include a reflecting element, a refracting element, a fiber diffuser, or any combination thereof, and a first light window positioned on the side surface portion. When light guides include a diverting feature configured to direct light within the light guide toward a side surface portion of the distal portion of the light guide, the light guides can also include at least a first light window positioned on a side surface portion of the light guide. In some embodiments the light windows span the entire circumference of the light guides, while in other embodiments the light windows only span a portion of the circumference of the light guides. Other properties of the light guides, including size, spacing, and distribution are described elsewhere herein.

In various embodiments, the light guides herein include one or more fiber diffusers. In some embodiments, a light guide can include a first fiber diffuser in a distal portion of the light guide, where the first fiber diffuser directs light from the light guide to exit the light guide at a side surface portion of the light guide. In cases where a light guide includes a first fiber diffuser to direct light from the light guide to exit the light guide at a side surface portion of the light guide, the side surface portion of the light guide is in optical communication with a first light window. In some embodiments the light windows span the entire circumference of the light guides, while in other embodiments the light windows only span a portion of the circumference of the light guides.

In yet other embodiments, the light guides herein can include a plurality of light windows and a plurality of fiber diffusers in the distal portion of the light guide. The plurality of light windows can include a first light window and the plurality of fiber diffusers can include the first fiber diffuser. Each fiber diffuser can direct light from the light guide to exit the light guide at a side surface portion of the light guide, where each side surface portion is in optical communication with one of the plurality of light windows. The plurality of light windows can be axially spaced apart with at least one intervening non-emitting portion of the light guide disposed between each of the plurality of light windows. The side surface portion can be a cylindrical side surface portion and a first light window can be configured as a cylindrical window.

Figure 43:
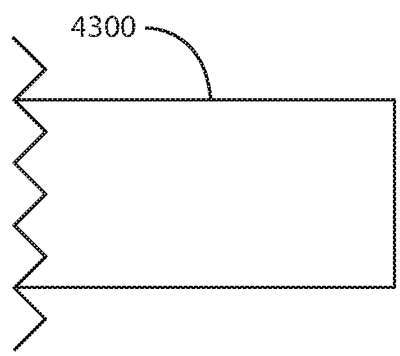
FIGS. 43-45 are schematic cross-sectional views of various embodiments of a distal portion of a light guide of a photoacoustic catheter in accordance with various embodiments herein.
Figure 44:
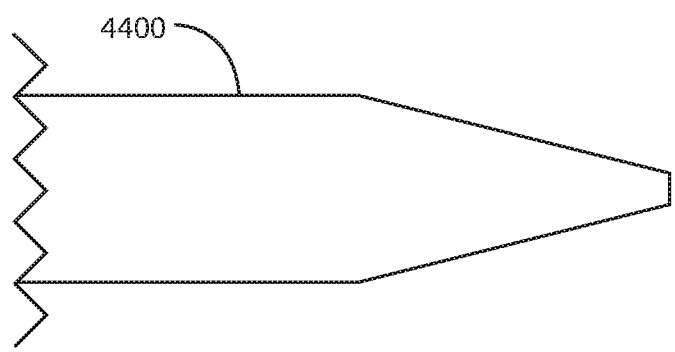
Figure 45:
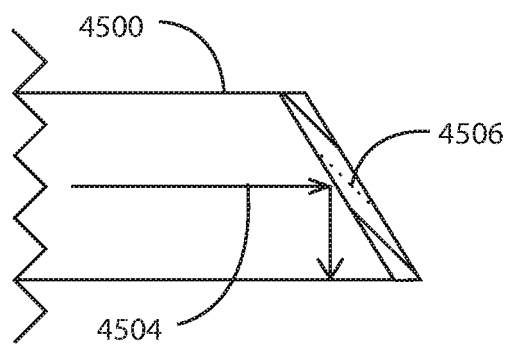

The light guides herein can include various configurations at a distal portion of the light guide. Referring now to FIGS. 43-45, schematic cross-sectional views of the distal portions of various shaped light guides are shown in accordance with various embodiments herein. In FIG. 43, a schematic cross-sectional view of a light guide 4300 is shown. Light guide 4300 includes a cylindrical end shape. In some embodiments, the end of the light guide can have a tapered shape. By way of example, in FIG. 44 a schematic cross-sectional view of a light guide 4400 having a tapered end shape is shown. In some embodiments, the end of the light guide can have an angled shape. By way of example, in FIG. 45 a schematic cross-sectional view of a light guide 4500 is shown. Light guide 4500 includes an angled end shape. The light guide 4500 also includes a diverting feature 4506 at the distal portion to direct the light 4504 within the light guide toward the side surface portion of the light guide. Light guide 4500 is configured such that light 4504 travels from a light source (not shown) in the direction from the proximal region of the light guide to the distal region of the light guide 4500, as indicated by the arrow. Upon contact with the diverting feature 4506, the light 4504 is diverted, or reflected, within the light guide 4500.

In some embodiments, a diverting feature can be included with the light guide to direct light toward a side surface portion of the distal portion of the light guide. A diverting feature can include any feature of the system herein that diverts light from the light guide away from its axial path toward a side surface portion of the light guide. Examples include a reflector, a refracting structure, and a fiber diffuser. Fiber diffusers will be discussed in more detail below.

In other embodiments, the light guides can form a spiral configuration about the longitudinal axis of the elongate shaft of the photoacoustic catheter. In some embodiments, the spiral configuration can run clockwise about the longitudinal axis of the elongate shaft of the photoacoustic catheter, while in other embodiments the spiral configuration can run counter-clockwise about the longitudinal axis of the elongate shaft of the photoacoustic catheter. In some embodiments, the light guides can form a single helix, a double helix, a triple helix, or a quadruple helix about the longitudinal axis of the elongate shaft of the photoacoustic catheter.

The light guides herein can come in various sizes and configurations. The light guides will have a longitudinal axis along the elongate shaft of the light guide and short axis about its circumference. In some embodiments, the light guides can have an outer diameter of about 100 μm, including the cladding and the core. In other embodiments, the light guides can include those that have an outer diameter of from 50 μm to 1000 μm including the cladding and the core. The length of the light guides can include those having a length of from 40 cm to 175 cm. In some embodiments, the length of the light guides can include those having a length of from 50-150 cm. In some embodiments, the length of the light guide can include those having a length of 40 cm, 50 cm, 60 cm, 70 cm, 80 cm, 90 cm, 100 cm, 125 cm, 150 cm, or 175 cm. It will be appreciated that the light guides herein can have a usable length that can fall within a range, wherein any of the forgoing lengths can serve as the lower or upper bound of the range, provided that the lower bound of the range is a value less than the upper bound of the range.

It will be appreciated that one or more light guides herein can be adhered to the outer surface of the elongate shaft of a catheter, to create a photoacoustic catheter. However, in other embodiments, one or more light guides can be disposed within a lumen of a photoacoustic catheter. In addition, the photoacoustic catheter may define a lumen for a guidewire having an inner diameter of about 0.014 inch (0.356 mm). In some embodiments, the photoacoustic catheter can include those having an inner diameter of about 0.018 inch (0.457 mm). In yet other embodiments, the photoacoustic catheter can include those having an inner diameter of about 0.035 inch (0.889 mm). In some embodiments the light guides herein can be integrated with a balloon catheter. In some embodiments the light guides herein can be integrated into a guide wire. In embodiments where the light guide is integrated into a guide wire, the resulting photoacoustic catheter can be used independently or can be used with various other balloon catheters.

Lumens of the Elongate Shaft (FIGS. 31-42)

The elongate shafts herein can include one or more lumens that span the length of the elongate shaft. Referring now to FIGS. 31-42, schematic cross-sectional views of various embodiments of an elongate shaft having multiple lumens are in accordance with various embodiments herein. In some embodiments, the elongate shaft can define a guidewire lumen. In some embodiments, the elongate shaft defines an inflation lumen surrounding the guidewire lumen, where the inflation lumen is in fluid communication with a balloon at a distal portion of the elongate shaft. In other embodiments, the elongate shaft defines an inflation lumen disposed alongside the guidewire lumen, where the inflation lumen is in fluid communication with a balloon at a distal portion of the elongate shaft. In yet other embodiments, the elongate shaft defines at least one control lumen and at least one light guide lumen.

Figure 31:
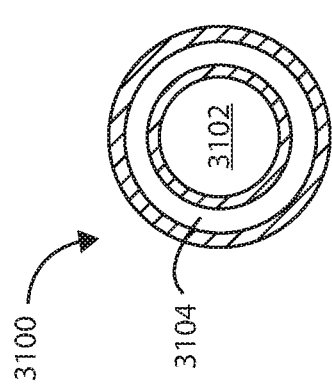
Figure 34:
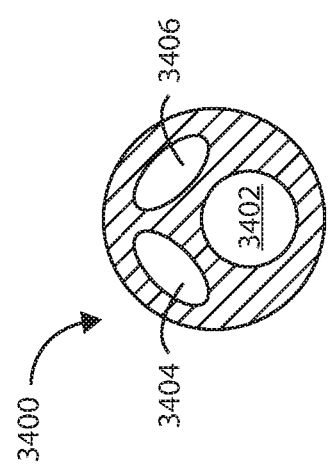
Figure 37:
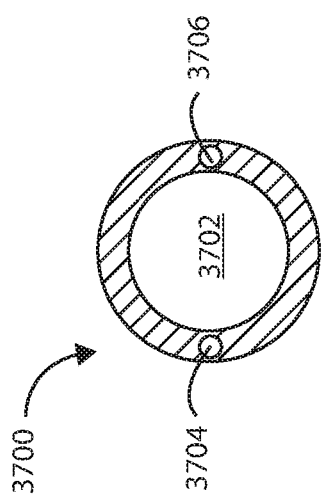
Figure 38:
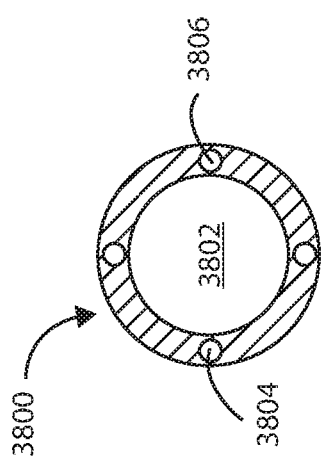
Figure 39:
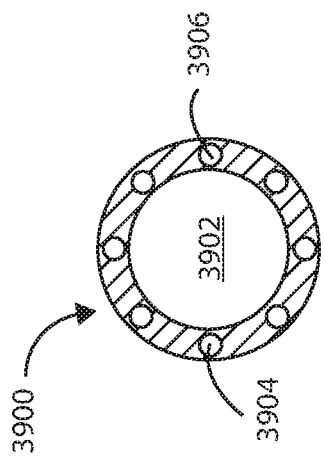
Figure 40:
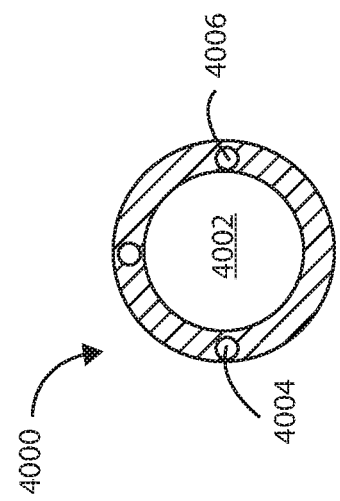
Figure 41:
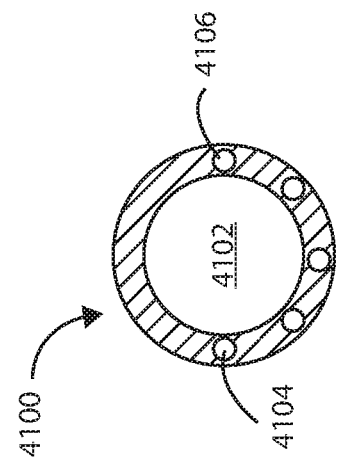
Figure 42:
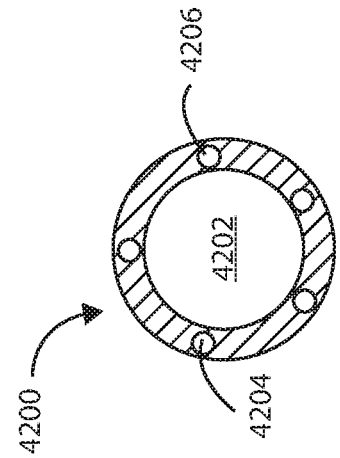

In the configuration in FIG. 31, elongate shaft 3100 includes concentrically disposed guidewire lumen 3102 and an inflation lumen 3104. In the configuration in FIG. 32, elongate shaft 3200 includes guidewire lumen 3202 and an inflation lumen 3204 disposed adjacent to and partially surrounding guidewire lumen 3202. In the configuration in FIG. 33, elongate shaft 3300 includes guidewire lumen 3302 and an inflation lumen 3304 disposed adjacent to guidewire lumen 3302. In the configuration in FIG. 34, elongate shaft 3400 includes guidewire lumen 3402, inflation lumen 3404, and a control lumen 3406. It will be appreciated that any of the control lumens described herein can be used for many purposes, including, but not to be limited to, blood flow, cooling or heating fluid flow, delivery of a diagnostic or therapeutic agent, a light guide lumen, an inflation lumen, and the like. In the configuration in FIG. 35, elongate shaft 3500 includes guidewire lumen 3502, inflation lumen 3504, and two control lumens 3506 and 3508. In the configuration in FIG. 36, elongate shaft 3600 includes guidewire lumen 3602, inflation lumen 3604, and control lumen 3606.

The light guides can be disposed within one or more light guide lumens disposed within the elongate shafts symmetrically about the circumference. In the configuration in FIG. 37, elongate shaft 3700 includes guidewire lumen 3702, light guide lumen 3704, and control lumen 3706. One or more of lumens 3702, 3704 and 3706 can serve as an inflation lumen. In the configuration in FIG. 38, elongate shaft 3800 includes guidewire lumen 3802, light guide lumen 3804, and control lumen 3806. Elongate shaft 3800 includes two additional lumens that can both be configured as light guide lumens, control lumens, or both a light guide lumen and control lumen. One or more of lumens 3802, 3804 and 3806 can serve as an inflation lumen. In the configuration in FIG. 39, elongate shaft 3900 includes guidewire lumen 3902, light guide lumen 3904, and control lumen 3906. Elongate shaft 3900 includes six additional lumens that can be configured as inflation lumens, light guide lumens, control lumens, or any combination of inflation lumens, light guide lumens and control lumens.

The light guides can be disposed within one or more light guide lumens disposed within the elongate shafts asymmetrically about the circumference. In the configuration in FIG. 40, elongate shaft 4000 includes guidewire lumen 4002, light guide lumen 4004, and control lumen 4006. Elongate shaft 4000 includes one additional lumen that can be configured as an inflation lumen, a light guide lumen or a control lumens. In the configuration in FIG. 41, elongate shaft 4100 includes guidewire lumen 4102, light guide lumen 4104, and control lumen 4106. Elongate shaft 4100 includes three additional lumens that can be configured as inflation lumens, light guide lumens, control lumens, or any combination of light guide lumens and control lumens. In the configuration in FIG. 42, elongate shaft 4200 includes guidewire lumen 4202, light guide lumen 4204, and control lumen 4206. Elongate shaft 4200 includes three additional lumens that can be configured as inflation lumens, light guide lumens, control lumens, or any combination of inflation lumens, light guide lumens and control lumens.

It will be appreciated that the lumens described in FIGS. 31-42 can assume many shapes, including, but not to be limited to, circular shape, square shape, crescent shape, triangular shape, and the like. The lumens of the elongate shafts can by symmetrically disturbed in the elongate shaft, asymmetrically distributed, or concentrically distributed. It will be further appreciated that the light guide lumens herein can be coated along the longitudinal length of the elongate shaft with a reflective material capable of propagating light along the elongate shaft from a distal light source to the proximal portion of the photoacoustic catheter.

Fiber Diffusers

A fiber diffuser directs light from within a light guide to exit at a side surface portion of the light guide. The fiber diffusers described herein can be created several ways. In some embodiments, the fiber diffusers can be created by micro-machining the surface of the distal portion of a light guide with a $CO_2$ laser. In some embodiments, a fused silica coating can be applied to the distal portion of the light guide. In other embodiments, the fiber diffuser can be formed from a glass, a polymer, or a metal coating on the distal portion of the light guide. In other embodiments, the fiber diffuser can be formed by a fiber Bragg grating on the distal portion of the light guide. In some embodiments, the fiber diffuser can include a machined portion of the light guide, a laser-machined portion of the light guide, fiber Bragg gratings, a fused splicing, a fused splicing forming at least one internal mirror, and a splicing of two or more diffuse regions. Suitable materials for a fiber diffuser can include, but not be limited to, the materials of the core or cladding, ground glass, silver coated glass, gold coated glass, TiO2, and other materials that will scatter and not significantly absorbed the light wavelength of interest. One method that can be used to create a uniform diffuser in a light guide, optical component, or materials is to utilize scattering centers on the order of 50 nanometers to 5 micrometers in size. The scattering centers can have a distribution around 200 nanometers in size.

Light Sources

The light sources suitable for use herein can include various types of light sources including lasers and lamps. Suitable lasers can include short pulse lasers on the nanosecond (ns) timescale. The lasers can also include short pulse lasers on the picosecond (ps), femtosecond (fs), and microsecond (us) timescales.

Exemplary nanosecond lasers can include those within the UV to IR spectrum, spanning wavelengths of about 10 nanometers to 10 millimeters. Nanosecond lasers can include those having repetition rates of up to 200 kHz. In some embodiments, the laser can include a Q-switched thulium:yttrium-aluminum-garnet (Tm:YAG) laser. In some embodiments, the laser can include a neodymium:YAG (Nd:YAG), holmium:YAG (Ho:YAG), erbium:YAG (Er:YAG), excimer laser, helium-neon laser, carbon dioxide laser, as well as doped, pulsed, fiber lasers.

Acoustic Pressure Waves

The photoacoustic catheters herein can generate acoustic pressure waves having pressures in the range of 2 megapascals (MPa) to 25 MPa. The maximum pressure generated by a particular photoacoustic catheter will depend on the light source, the absorbing material, the propagation medium, a distance of the measurement device to the source of the pressure wave, and any other relevant factors. In some embodiments, the photoacoustic catheters herein can generate acoustic pressure waves having peak or maximum pressures in the range of 5 MPa to 20 MPa. In some embodiments, the photoacoustic catheters herein can generate acoustic pressure waves having peak pressures of about 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, or 25 MPa. It will be appreciated that photoacoustic catheters herein can generate acoustic pressure waves having operating pressures or peak pressures that can fall within a range, wherein any of the forgoing numbers can serve as the lower or upper bound of the range, provided that the lower bound of the range is a value less than the upper bound of the range.

Therapeutic treatment can act via a fatigue mechanism or a brute force mechanism. For a fatigue mechanism, operating pressures would be about 0.5 MPa to 2 MPa, or about 1 MPa. For a brute force mechanism, operating pressures would be about 20 MPa to 30 MPa, or about 25 MPa. Pressures between the extreme ends of these two ranges may act upon a calcified lesion using a combination of a fatigue mechanism and a brute force mechanism.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

What is claimed is:

1. A photoacoustic catheter adapted for placement within a blood vessel having a vessel wall, the photoacoustic catheter comprising:
    an elongate shaft extending between a proximal region and a distal region, the elongate shaft comprising a light guide that is in optical communication with a light source;
    a balloon coupled to the elongate shaft, the balloon selectively expanding from a collapsed configuration suitable for advancing the photoacoustic catheter through a patient's vasculature to a first expanded configuration suitable for anchoring the balloon in position relative to a treatment site; and
    a photoacoustic transducer disposed on a surface of the balloon and in optical communication with the light guide, the photoacoustic transducer comprising a light-absorbing material and a thermal expansion material;
    wherein a distal portion of the light guide includes a diffraction grating pattern configured to direct light from the light guide to one or more light pattern locations when the balloon is in the first expanded configuration;
    wherein a wall of the balloon comprises integrated fluid bubbles.

2. The photoacoustic catheter of claim 1, wherein the photoacoustic transducer is located on one of: (i) an outer surface of the balloon, and (ii) an inner surface of the balloon.

3. The photoacoustic catheter of claim 1, wherein the photoacoustic transducer comprises a conformal coating on a surface of the balloon, the conformal coating extending continuously between a proximal location and a distal location on the surface of the balloon, the conformal coating extending continuously around a circumference of the balloon.

4. The photoacoustic catheter of claim 1, wherein the photoacoustic transducer is configured as a plurality of at least one of: (i) circumferential bars, (ii) longitudinal bars, (iii) diagonal bars, and (iv) islands.

5. The photoacoustic catheter of claim 1, wherein the balloon is configured to change from the first expanded configuration to a second, further expanded configuration.

6. The photoacoustic catheter of claim 1, wherein the thermal expansion material of the photoacoustic transducer includes a polymer that is in thermal contact with the light absorbing material.

7. The photoacoustic catheter of claim 1, wherein the balloon is an outer balloon, the photoacoustic catheter further comprising a second, inner balloon coupled to the elongate shaft within the outer balloon, the inner balloon being configured to expand from a collapsed configuration suitable for advancing the photoacoustic catheter through the patient's vasculature to a first expanded configuration, the inner balloon comprising the photoacoustic transducer disposed on a surface of the inner balloon; the outer balloon being configured to expand using an outer balloon inflation fluid, and the inner balloon being configured to expand using an inner balloon inflation fluid.

8. The catheter of claim 7, wherein the outer balloon inflation fluid is a liquid and the inner balloon inflation fluid is a gas.

9. The photoacoustic catheter of claim 7, wherein the inner balloon includes a concave portion when the inner balloon is in the first expanded configuration, the photoacoustic transducer being located on an outer surface of the inner balloon, and the concave portion being configured to focus at least one acoustic pressure wave from the photoacoustic transducer.

10. The photoacoustic catheter of claim 1 wherein the thermal expansion material is selected from a group consisting of polydimethylsiloxane (PDMS), polytetrafluoroethylene (PTFE), polyimide, polyisobutylene (PIB), PIB polyurethane, polyurethanes, styrene isoprene butadiene, ethylene propylene polyacrylic, ethylene acrylic, fluorosilicone, polybutadiene, polyisoprene, and thermoplastic elastomers.

11. The photoacoustic catheter of claim 10 wherein the light-absorbing material is selected from a group consisting of nanoparticles, carbon nanotubes, candle soot, candle soot nanoparticles, carbon black, a nanotube array, multiwall carbon nanotubes, and light absorbing dye.

12. The photoacoustic catheter of claim 1 wherein the light guide is an optical fiber and the light source is a laser.

13. The photoacoustic catheter of claim 1 wherein the thermal expansion material includes a metallic film.

14. The photoacoustic catheter of claim 1 wherein the thermal expansion material includes at least one of silver, copper, gold, aluminum, beryllium, tungsten, and magnesium.

15. A photoacoustic catheter adapted for placement within a blood vessel having a vessel wall, the photoacoustic catheter comprising:
an elongate shaft extending between a proximal region and a distal region, the elongate shaft comprising a light guide that is in optical communication with a light source;
a balloon coupled to the elongate shaft, the balloon selectively expanding from a collapsed configuration suitable for advancing the photoacoustic catheter through a patient's vasculature to a first expanded configuration suitable for anchoring the balloon in position relative to a treatment site; and
a photoacoustic transducer disposed on a surface of the balloon and in optical communication with the light guide, the photoacoustic transducer comprising a light-absorbing material and a thermal expansion material;
wherein the thermal expansion material and the light-absorbing material are positioned adjacent to one another in layers;
wherein a wall of the balloon comprises integrated fluid bubbles.

16. A photoacoustic catheter adapted for placement within a blood vessel having a vessel wall, the photoacoustic catheter comprising:
an elongate shaft extending between a proximal region and a distal region, the elongate shaft comprising a light guide that is in optical communication with a light source;
a balloon coupled to the elongate shaft, the balloon selectively expanding from a collapsed configuration suitable for advancing the photoacoustic catheter through a patient's vasculature to a first expanded configuration suitable for anchoring the balloon in position relative to a treatment site; and
a photoacoustic transducer disposed on a surface of the balloon and in optical communication with the light guide, the photoacoustic transducer comprising a light-absorbing material and a thermal expansion material;
wherein a distal portion of the light guide includes a diffraction grating pattern configured to direct light from the light guide to one or more light pattern locations when the balloon is in the first expanded configuration;
wherein the thermal expansion material and the light-absorbing material are positioned adjacent to one another in layers to form a composite film around the balloon;
wherein a wall of the balloon comprises integrated fluid bubbles.

17. The photoacoustic catheter of claim 16 wherein a layer of the light-absorbing material is disposed on the balloon in optical contact with a core of the light guide.

18. The photoacoustic catheter of claim 16 wherein a layer of the thermal expansion material is disposed on a surface of the light-absorbing material at an outermost surface.

19. The photoacoustic catheter of claim 16 wherein the thermal expansion material is in a matrix with the light absorbing material.

20. The photoacoustic catheter of claim 16 wherein the light-absorbing material and the thermal expansion material are individually applied to the balloon.

\* \* \* \* \*